(12) United States Patent
Marks

(10) Patent No.: US 7,596,578 B1
(45) Date of Patent: *Sep. 29, 2009

(54) METHOD AND APPARATUS FOR OPERATING AND FUNDING A QUESTION AND ANSWER INTERACTIVE SYSTEM

(75) Inventor: James D. Marks, New York, NY (US)

(73) Assignee: Expert Viewpoint, LLC, New York, NY (US)

( * ) Notice: Subject to any disclaimer, the term of this patent is extended or adjusted under 35 U.S.C. 154(b) by 492 days.

This patent is subject to a terminal disclaimer.

(21) Appl. No.: 09/603,601

(22) Filed: Jun. 26, 2000

Related U.S. Application Data

(63) Continuation-in-part of application No. 09/516,996, filed on Mar. 1, 2000, now abandoned, which is a continuation-in-part of application No. 09/447,259, filed on Nov. 23, 1999, now Pat. No. 7,472,071.

(51) Int. Cl.
*G06F 17/00* (2006.01)
*G06F 7/00* (2006.01)
*G06F 9/46* (2006.01)
*G05B 19/418* (2006.01)
*G06Q 30/00* (2006.01)
*G07G 1/14* (2006.01)

(52) U.S. Cl. .......................... 707/104.1; 705/2; 705/14
(58) Field of Classification Search ................. 600/300, 600/301; 705/2, 14, 8; 345/758; 707/104.1
See application file for complete search history.

(56) References Cited

U.S. PATENT DOCUMENTS 5,005,143 A 4/1991 Altschuler et al.
(Continued)

FOREIGN PATENT DOCUMENTS

DE 19812167 9/1999

WO WO 9804061 A1 1/1998
WO WO 2001 39076 5/2001

OTHER PUBLICATIONS

Screenshots from the website The Body.com. Obtained from www.archive.org. Screenshots archived on Mar. 4, 1998.*

(Continued)

*Primary Examiner*—James Trujillo
*Assistant Examiner*—Jeffrey A Burke
(74) *Attorney, Agent, or Firm*—Darby & Darby PC

(57) ABSTRACT

A method and system, executed by a server, is disclosed for receiving questions from users regarding one or more topics and providing answers from a set of experts. Users can direct questions to one or more specific experts, who in turn can answer the questions, refer the questions to other experts, or both. The server automatically organizes and stores questions and answers in various for a dedicated to one or more topics, such as medical treatment for specific health conditions. Responses generated by the experts to the questions asked by the users may, in turn, be reviewed by peer review personnel. The system may be deployed at multiple network sites to provide a question and answer forum to users who visit different sites. Each network site in which the system is deployed may selectively decide whether to post at its network site the responses by experts and/or peer review personnel to questions originating from other network sites. In addition, each network site can selectively decide whether the responses by experts and/or peer review personnel to questions originating at their network site should be permitted to be posted on other network sites. Methods for funding a network site according to the present invention include the provision of advertising banners, receiving subscription payments or fees from user/subscribers for receiving expert opinions, and receiving payments from third party sponsors. Users who access the site may, in turn, receive benefits in exchange for soliciting such expert opinions.

28 Claims, 31 Drawing Sheets

U.S. PATENT DOCUMENTS

| | | | |
|---|---|---|---|
| 5,517,405 A | 5/1996 | McAndrew et al. | 364/401 |
| 5,689,641 A | 11/1997 | Ludwig et al. | |
| 5,794,219 A | 8/1998 | Brown | 705/37 |
| 5,819,267 A | 10/1998 | Uyama | 707/6 |
| 5,862,223 A | 1/1999 | Walker et al. | 380/25 |
| 5,875,327 A | 2/1999 | Brandt et al. | |
| 5,880,731 A * | 3/1999 | Liles et al. | 345/758 |
| 5,890,149 A | 3/1999 | Schmonsees | |
| 5,948,054 A | 9/1999 | Nielsen | |
| 5,967,789 A | 10/1999 | Segel et al. | 434/236 |
| 6,026,148 A | 2/2000 | Dworkin et al. | 379/88.18 |
| 6,026,396 A | 2/2000 | Hall | 707/4 |
| 6,039,688 A * | 3/2000 | Douglas et al. | 600/300 |
| 6,058,395 A | 5/2000 | Buzaglo et al. | |
| 6,076,100 A | 6/2000 | Cottrille et al. | 709/203 |
| 6,085,176 A | 7/2000 | Woolston | |
| 6,122,632 A * | 9/2000 | Botts et al. | 707/10 |
| 6,209,100 B1 | 3/2001 | Robertson et al. | |
| 6,223,165 B1 | 4/2001 | Lauffer | |
| 6,526,404 B1 * | 2/2003 | Slater et al. | 707/5 |
| 6,537,213 B2 | 3/2003 | Dodds | |
| 6,643,660 B1 | 11/2003 | Miller et al. | |
| 6,658,467 B1 * | 12/2003 | Rice et al. | 709/224 |
| 6,691,159 B1 * | 2/2004 | Grewal et al. | 709/219 |
| 6,938,068 B1 * | 8/2005 | Kraft et al. | 709/203 |
| 7,167,855 B1 * | 1/2007 | Koenig | 707/3 |
| 7,376,700 B1 * | 5/2008 | Clark et al. | 709/204 |
| 2003/0088461 A1 * | 5/2003 | Christensen | 705/14 |
| 2003/0163356 A1 * | 8/2003 | Marks et al. | 705/7 |
| 2003/0177030 A1 | 9/2003 | Turner et al. | |
| 2004/0030781 A1 | 2/2004 | Etesse et al. | |
| 2006/0111943 A1 * | 5/2006 | Wu | 705/3 |
| 2008/0108881 A1 * | 5/2008 | Stupp et al. | 600/300 |

OTHER PUBLICATIONS

Metze, Florian et al., "The Spree Exepert Finding System", International Conference on Semantic Computing, 2007.*
C. Hodgson, "Online expert databases and services," *Econtent*, v22, n6, p. 58-53, Dec. 1999.
M. Whitehead, "Advice Sites," *Internet Magazine*, Jun. 2000.
L. Teschler, "Advice On-line for Engineers," *Machine Design*, Jan. 14, 1999.
Hill, Scott. "There's Nothing Else Out There Like It: WebBoard Users Tell Why." *WebBoard.com* [online], Jan. 2000.
Figallo, Cliff. "Hosting Web Communities: Building Relationships, Increasing Customer." *Internet World* [online], 1998.
The web site "www.intelihealth.com".
"Do Sponsors Sway Health Web Sites?", *Wall Street Journal*, Feb. 8, 2000.
The web site "www.broaddaylight.com".
The web site "www.medformation.com".
The web site "www.exp.com".
The web site "www.experts.com".
The web site "www.inforocket.com".
The web site "www.askme.com".
The web site "www.expertcenteral.com".
The web site "www.frenzi.com".
The web site "www.knowpost.com".
The web site "www.keen.com".
The web site "www.ehow.com".
Coppeto, et al., Project Athena, Massachusetts Institute of Technology, 1989.

* cited by examiner

FIG. 3

THE BODY: AN AIDS AND HIV INFORMATION RESOURCE

 INSIGHT FROM EXPERTS | HOME

This page is sponsored in part by

  

  

Learn more from America's leading experts and columnists working on AIDS/HIV.

| Q&A | Your personal questions answered on a variety of topics in The Body's Interactive Q&A Forums: | TREATMENT with Cal Cohen, M.D., M.S. Judith S. Currier, M.D., M.Sc. | FATIGUE AND ANEMIA with J. B. Molaghan, NP, ACRN |
|---|---|---|---|
| |  Ask Rev. Steve Pieters your questions about HIV and spiritual support | ORAL HEALTH with David A. Reznik, DDS | OPPORTUNISTIC INFECTIONS with Judith S. Currier, M.D., M.Sc. |
| | | WASTING, DIET NUTRITION AND EXERCISE with Douglas Dieterich, M.D. Alvan Fisher, M.D. Marc Hellerstein, M.D., Ph.D. | VIRAL LOAD AND RESISTANCE with Mark Holodniy, M.D., FACP, CIC |
| | | MIXED-HIV-STATUS COUPLES with Robert H. Remien, Ph.D. | MENTAL HEALTH with Michael Shernoff, MSW |
| | | | SAFE SEX AND TRANSMISSION with Rick Sowadsky, MSPH |
| | | SPIRITUAL SUPPORT with The Rev. A. Stephen Pieters Father Rodney J. DeMartini | WORKPLACE ISSUES with Nancy Breuer Lynn L. Franzoi |

FIG. 4

THE BODY: AN AIDS AND HIV INFORMATION RESOURCE

 TREATMENT FORUM [HOME]

Disclaimer | To volunteer for clinical studies, click here.

Welcome to The Body's Treatment Forum. We are pleased to feature three outstanding HIV/AIDS specialists to answer your treatment questions: Cal Cohen, M.D., M.S., Judith S. Currier, M.D., M.Sc., and Andrew T. Pavia, M.D.

      

Cal Cohen, M.D., M.S.  Judith S. Currier, M.D., M.Sc.  Andrew T. Pavia, M.D.
Harvard Medical         University of                   University of Utah
School                  California, Los Angeles         School of Medicine
                        School of Medicine From the beginning of the epidemic, these specialists have worked extensively with HIV/AIDS patients, either heading major American AIDS clinics or research facilities; they also see patients and teach other physicians. We invite you to draw on their exceptional expertise in HIV/AIDS treatment issues.

Read answered questions | Add your question to the list.

Worried if you are infected? Have a question on transmission/exposure/safe sex? Click here.

*Please Note:* Due to volume considerations, not all questions can be answered. Questions most likely to be answered will be those of general interest to a broad group of visitors to this forum. Questions pertaining to a specific case; requests for diagnosis, medical advice or second opinion; or requests for opinions about untested alternative therapies will generally not be answered.

Before posting a question, please read through recently answered questions below and answers archived by category at the end of this page. The doctors have already responded to a variety of questions and you may discover several that address your concerns.

For questions related to transmission or testing, please see The Body's Forum on Safe Sex and HIV Prevention. For questions on fatigue and/or anemia, please see The Body's Forum on Fatigue and Anemia. For questions on viral load and resistance testing, please see The Body's Forum on Viral Load and Resistance Testing. The participation of Drs. Cal Cohen and Judith Currier in this Treatment Forum is made possible by unrestricted educational grants from Bristol-Myers Squibb Immunology, Roxane Laboratories, Inc., and Merck & Co., Inc.

Answers to Recent Treatment Questions:

- HIV and malaria, yellow fever vaccine (November 19, 1999)
- TESTING FOR ILLEGAL DRUGS (November 19, 1999)

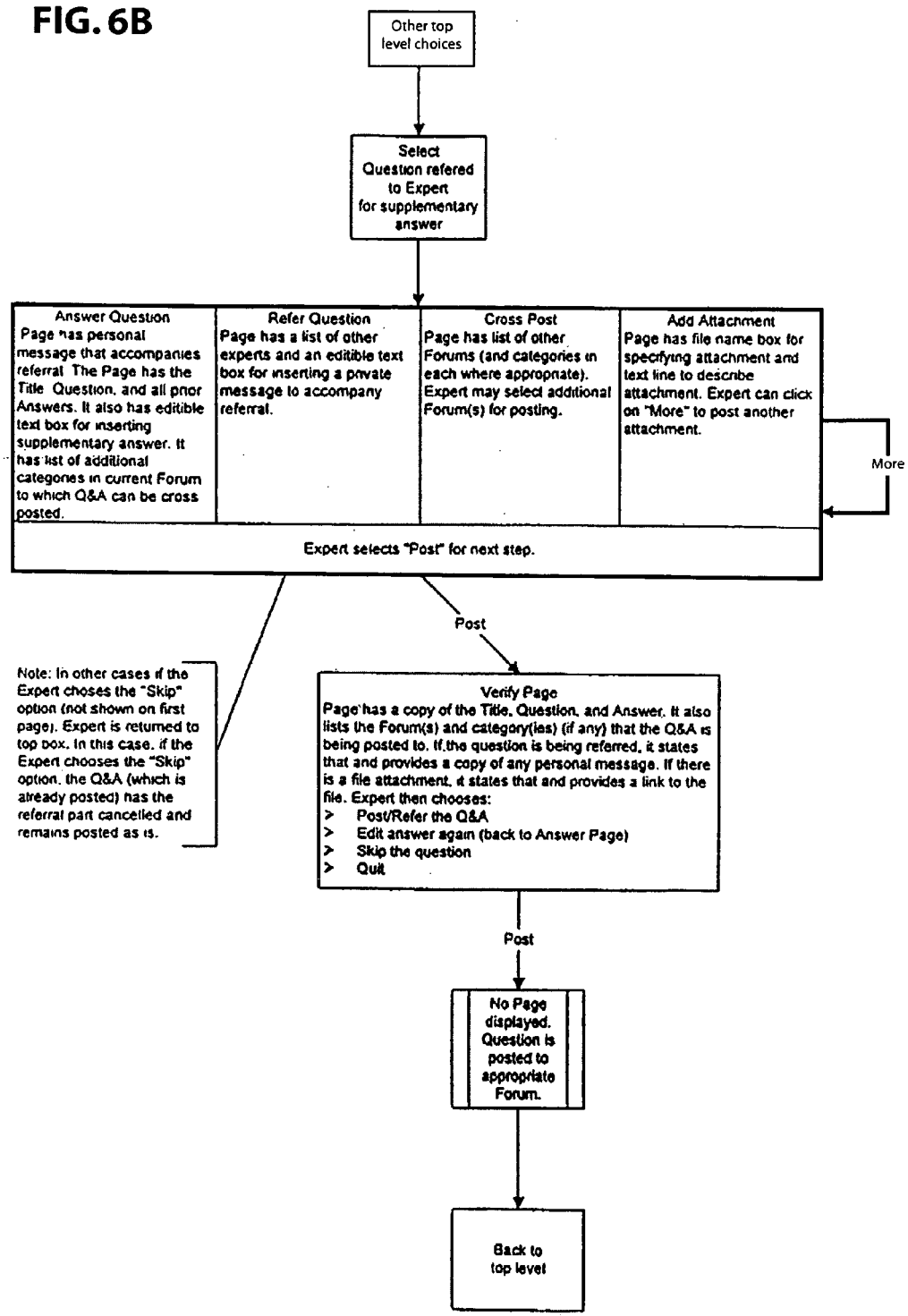

FIG. 7

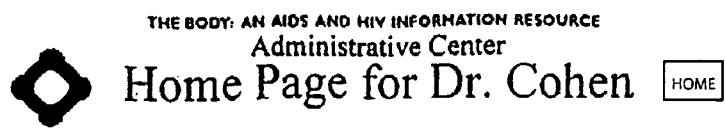

THE BODY: AN AIDS AND HIV INFORMATION RESOURCE
Administrative Center
Home Page for Dr. Cohen [HOME]

Hello, Dr. Cohen! There are currently 1118 question(s) awaiting answers from you. Please choose one of the following:

[REFER] Answer one or more of 10 questions referred to you by your colleagues.

[SUPPLEMENT] Provide a supplementary answer to one or more of 3 questions and answers referred to you by your colleagues.

[FOR ME] Answer one or more of 105 questions directed to you from the public through the Treatment Forum.

[GENERAL] Answer one or more of the 1000 questions directed to any doctor from the public through the Treatment Forum.

Or else select one of the following options:

[EDIT] Edit your answers to previous questions.

[QUIT] Quit the administrative center and return to the public portion of The Body.

Questions referred to you by your colleagues:

Questions sent to any doctor from the public at the Treatment Forum

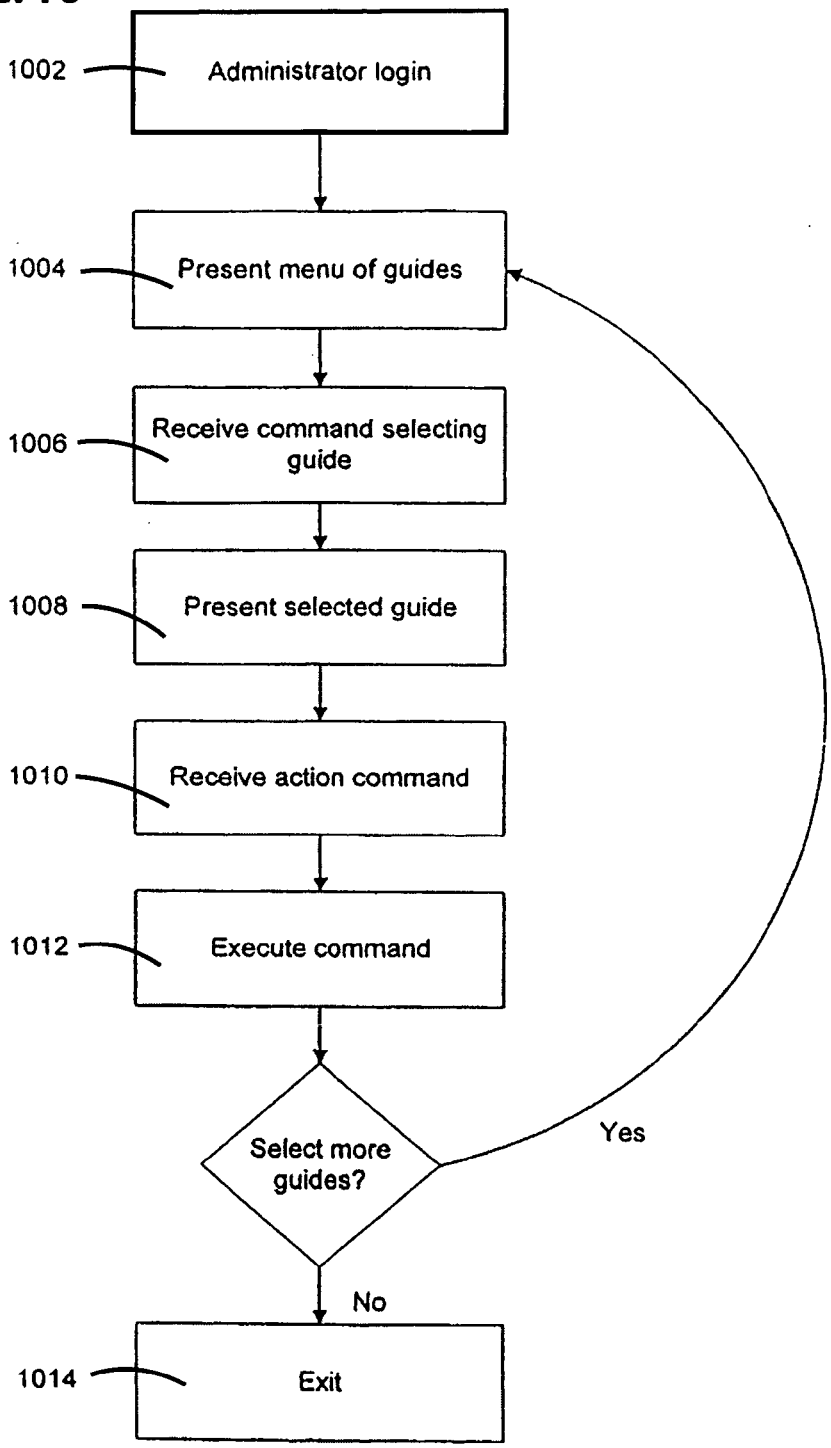

FIG. 12

THE BODY: AN AIDS AND HIV INFORMATION RESOURCE
Administrative Center
Welcome Joanne          [HOME]

General Operations

| CONFIGURE SYSTEM | Configure Whole System |

| ADD FORUM | Add A New Forum |

| KILL SESSION | Kill A Session |

| VIEW ADDITIONS | View Additions |

Personnel Operations

| ADD ADMINISTRATOR | Add an Administrator |

| ADD EXPERT | Add an Expert. |

Select An Expert For Edit [▼]

| EDIT EXPERT | Edit / Delete This Expert. |

Select An Administrator For Deletion [▼]

| DELETE ADMINISTRATOR | Delete This Administrator. |

Operations On a Specific Forum

Select A Forum To Work On [▼]

| CONFIGURE FORUM | Configure (Edit) A Forum |

| CONFIGURE GROUP | Configure Group (Archive or Current) |

| ADD CATEGORY | Add A Category |

| CONFIGURE CATEGORY | Configure (Edit) Category |

| EDIT Q & A | Edit Question And Answer |

Change My Password

Old Password: _____

New Password: _____

New Password: (again): _____

| CHANGE PASSWORD |

[ QUIT ]

METHOD AND APPARATUS FOR OPERATING AND FUNDING A QUESTION AND ANSWER INTERACTIVE SYSTEM

CROSS REFERENCE TO RELATED APPLICATIONS

This application is a continuation-in-part of U.S. patent application Ser. No. 09/516,996, filed Mar. 1, 2000, now abandoned, which is a continuation-in-part of U.S. patent application Ser. No. 09/447,259 filed on Nov. 23, 1999, having issued on Aug. 26, 2008 as U.S. Pat. No. 7,472,071. The entireties of both applications are hereby incorporated by reference herein.

FIELD OF THE INVENTION

The present invention relates to data processing for business practices, and relates more particularly to methods and apparatus for operating and funding an interactive network site.

DESCRIPTION OF THE RELATED ART

In an interactive system, a user may engage in a dialog with a system through a series of interactions with the system, and the dialog results in changes to the system's behavior. Many World Wide Web sites are interactive. In contrast to static systems, where users simply read information posted on site, interactive web sites allow users to alter a site's contents or behavior. Interactive web sites provide a unique opportunity for interaction between users and experts in a certain field. For example, in a question and answer exchange, a user can pose questions and receive answers from an expert, using an interactive web site to facilitate the exchange.

One problem with traditional interactive web sites is the difficulty in modifying them. These systems require system administrators and technical staff to control the interaction between users and administrators. Expensive staff members have to undertake tedious and repetitive tasks, such as archiving older messages and deleting unanswered questions. Systems and methods consistent with the current invention automate these administrative tasks, freeing up staff members to concentrate on aspects of the systems that require judgment and discretion.

A problem with existing interactive systems which use experts is the lack of flexibility available to experts when answering questions. Some question and answer web sites, such as "Frenzi.com" provide the user with three responses from different experts to each question that is asked. Each expert can only give a single response. When experts can give only one answer to a question, it is difficult to change an opinion or elaborate on an answer. Systems and methods consistent with the current invention give experts a great deal of flexibility and control. Experts can add references and pictures to their answer. They can refer questions to other peer review personnel or supplement or edit their previous answers. Experts can also post multiple answers to a single question. These capabilities help experts make their responses more accurate and complete.

Further problems with such systems include the ability to fund the operation of the network site and to compensate experts employed by the site administrator. Existing question and answer interactive network sites rely on various funding techniques. Experts that are answering the questions may charge the users a fee. This is the situation at the "ExpertCentral.com" network site in which the experts ask for a fee or submit proposals for a project to the user. The site in turn takes a percentage of all fees paid to the experts. Alternatively, the "AskMe.com" web site is a free consumer-to-consumer service that allows consumers to ask any question to real people with expertise in a broad range of topics. A bonus point system distributes money each month to the top rated experts and users. Another common method of funding the web site is to issue points or credits to experts and/or users. Users are issued a predetermined number of initial credits. Each time the user's question is answered the system deducts some of those credits. Credits may be earned by answering other users' questions.

It is therefore desirable to develop other methods of funding that shift at least some of the financial burden off of the user and/or expert to a third party sponsor. Not only is the third party sponsor typically in a better financial position to bear some, if not all, of the financial burden, but the business operations of the third party sponsor may benefit as a result of funding the forum.

SUMMARY THE INVENTION

In order to address and solve certain of the foregoing shortcomings in the prior art, the present invention provides a method and accompanying system for funding an interactive network site that provides one or more fora accessible by users and experts. Each forum preferably relates to a particular topic, such as a medical topic. An operator of the network site may then receive a payment from a third party wherein the payment is conditioned upon the topic.

In a second embodiment of the present invention, a method and accompanying apparatus for reviewing medical treatment of a user receiving medical insurance includes providing a forum on a network site for access by a user and an expert, wherein the user may request an opinion of the expert, which in turn may be peer-reviewed by a second expert providing a second opinion on a medical treatment received by the user. The user may then have their health insurance premium adjusted based on the request.

In another embodiment, topics may include discussions regarding a particular medical condition, the use of a drug or a medical treatment. The third party may be any party interested in the topic such as a medical insurance provider or a drug manufacturer.

In a further embodiment of the present invention, the expert may include a doctor, an insurance case manager, or other medical personnel.

In yet another embodiment, the operator of the network site may charge a fee to the user for the access. The fee, in turn, may be a subscription fee or may be charged based on each transaction the user has with the network site. The payment of the fee charged to the user may be provided by a third party in exchange for the user providing personal information to the third party or to the network site to be aggregated for the third party without release of the user's identity. Such personal information may include demographic information, identification information, medical treatment information and drug treatment information.

In still another embodiment, the site operator may display banner advertisements on a page of the network site and receive a fee in exchange for the same. In this embodiment, the fee may be based on a number of users accessing the network site.

In still another embodiment of the present invention, an expert may be compensated for responding to one or more questions presented to the forum.

In yet another embodiment of the present invention, the network site provides peer review for a response submitted by an expert. The peer review may be performed by a doctor or an insurance case manager.

In still another embodiment of the present invention, the user may be a medical professional and the topic may be based on a continuing medical education course.

In yet another embodiment of the present invention, a user may receive points for accessing one or more network sites, including the network site. In turn, the user may receive a benefit from the third party based on the accumulated points the user receives. Benefits may include providing access to the forum, providing a payment of a fee for accessing the site, providing a discount on a medical treatment, providing a discount on a drug and providing a discount on a medical insurance premium. The points may be awarded to the user based on a number of visits the user made to a network site, an answer to at least one question provided by the user, and a provision of personal information from the user.

In still another embodiment of the present invention, a user may be provided with a user identification and a password in order to access the network site.

In yet another embodiment, the method and accompanying apparatus for reviewing medical treatment of a user receiving medical insurance includes providing a forum on a network site for access by a user and an expert, wherein the user may request an opinion of the expert, which in turn may be peer-reviewed by a second expert providing a second opinion on a medical treatment received by the user. The user may then have their health insurance premium adjusted based on the request.

In another embodiment, a method for funding a question and answer interactive network site is provided, wherein a payment is received from a third party, e.g., an HMO provider, associated with a third party service for access to the network site by only those users that subscribe to the third party service.

In still another embodiment, a method for funding an interactive network site is provided, wherein experts respond to questions asked by users. In turn, peer review personnel review the responses provided by the experts. Funding for the provision of the forum is received through third party payments.

While in another embodiment, a method for funding an interactive network site is provided, wherein payments for the provision of the forum are received from a third party associated with a third party service. Benefits concerning the third party service are issued to the user by the third party. Alternatively, benefits may be issued to a party other than the third party, such as a pharmacy.

In still another embodiment, a method for reviewing medical treatment of a user enrolled in a medical insurance program is provided. In response to a request, the user receives a second opinion from the expert concerning a medical treatment and/or a drug. Subsequently, the user's insurance premium is adjusted.

Another embodiment of the invention is directed to a method for operating a question and answer forum system deployed at a plurality of interactive network sites. A question is received from a user accessing one of said plural interactive network sites. Thereafter, an answer is received from an expert in response to the question along with a command signal indicating which network sites to post the response. The response generated by the expert is then posted on a selective basis on any of the plural interactive network sites based on the command signal. Also disclosed is a system for providing the question and answer forum described above.

The present invention is also directed to a method for operating a question and answer forum system deployed at a plurality of interactive network sites, wherein questions and responses are received from users and experts, respectively. A command signal is received from a server associated with at least one of the network sites. The responses generated by the experts are posted on a selective basis at the interactive network sites based on the command signal. Also disclosed is a system for providing the question and answer forum above.

Another embodiment discloses a method for funding an interactive network site, wherein responses by experts to questions generated by users are, in turn, reviewed by peer review personnel. A payment is received from a third party for the provision of the forum.

BRIEF DESCRIPTION OF THE DRAWINGS

Further aspects of the instant invention will be more readily appreciated upon review of the detailed description of the preferred embodiments included below when taken in conjunction with the accompanying drawings, of which:

FIG. 3 is an example of a home page which offers a user a choice of several fora;

FIG. 4 is an example of a forum page for the treatment forum as it appears at a user interface;

FIGS. 6A-C depict a flow chart showing one implementation of an expert's interaction in detail;

FIG. 7 is an example of how an expert home page appears on an expert interface;

FIG. 10 is a flow chart showing the interaction between the system and an administrator;

FIG. 12 is an example of how an administrator's home page appears on an administrator's interface;

DETAILED DESCRIPTION OF THE PREFERRED EMBODIMENT

Systems and methods consistent with the present invention allow users to obtain information on a given subject by interacting with experts on that subject. Users can get answers to their questions either by asking a question or by reviewing answers to questions that others have posed. If asked a question, an expert can either provide an answer or refer the question to another expert. An expert can also act as peer review personnel by reviewing the responses posted by another expert. In addition, experts and/or peer review personnel can post their responses in any forum, category, and network site they desire.

In one embodiment, users can visit a web site to have their AIDS- and HIV-related questions answered by doctors and other experts in the field. The site provides several benefits to users. For instance, it lowers barriers between patients and clinicians, demystifies HIV/AIDS and its treatment, improves patients' quality of life and fosters community through human connection.

The web site is divided into several fora based on subject matter within the broad topic of AIDS- and HIV-related information. Fora may have separate sections for recent questions and archived, or older, questions. The archived questions for a particular fora may be further divided into categories by subject matter. Each forum may have its own set of categories.

One possible implementation provides for dynamic management of each forum and of the system itself. If individual forum pages are properly designed, system administrators can make changes to the web site without using a low-level programming language, such as PERL, because system software automatically "manages" the questions and answers. The system itself stores questions and answers, handles categorizations, makes the distinction between current and archived questions, allows creation and editing of pages, and manages the experts and their interrelationships.

Dynamic management of the system may be achieved using flexible "templates" instead of standard, fixed HTML documents to create the web pages. These templates may serve as a basis for only one page (e.g., the home page for the treatment forum) or for hundreds of pages (e.g., the layout for the questions and answer pages). Templates differ from ordinary HTML pages in that they include commands that return information about parts of the system. These commands take the form of a standard interface to the low-level language (e.g., PERL) part of the system. By using these commands, administrators can change sections of the system easily, quickly, and without having to write or change low-level code.

Figure 1:
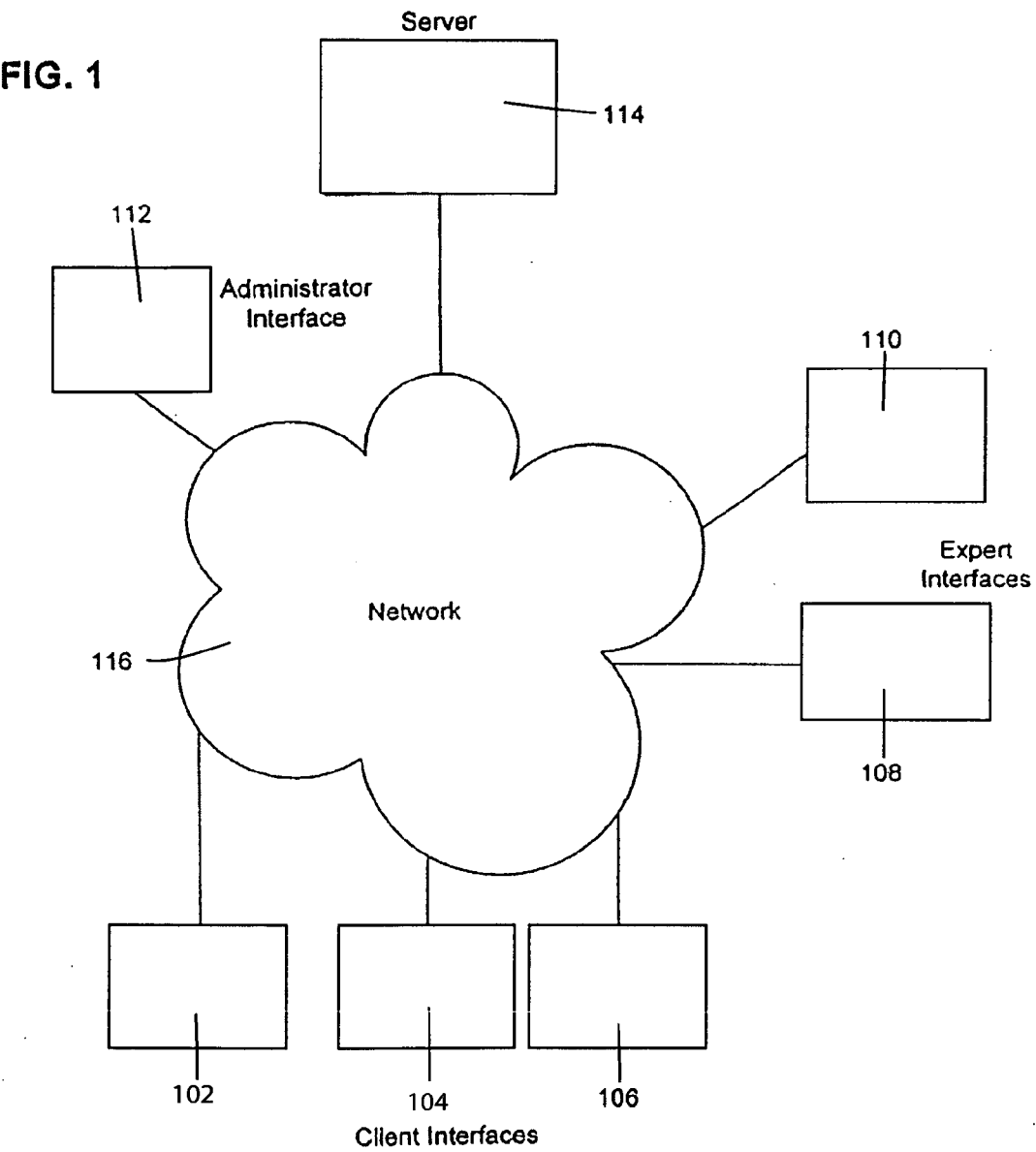
FIG. 1 depicts an information-sharing system consistent with the present invention.

FIG. 1 depicts an information-sharing system 100 consistent with the present invention. System 100 includes a number of devices such as computers 102, 104 and 106, with client interfaces, computers 108 and 110 with expert interfaces, computer 112 with an administrator's interface, and server 114. Computers 102, 104, 106, 108, 110 and 112, and server 114 communicate via network 116. Network 116 could be, for example, the Internet, an intranet, a local area network (LAN), a wide area network (WAN), a bulletin board system (BBS) implemented on a public switched telephone network, a wireless network, or any other suitable telecommunications or computer network. Although FIG. 1 shows a specific number of devices one skilled in the art will recognize that any number of devices could be connected to network 116 without departing from the principles of the present invention. Furthermore, although only one server 114 is displayed, it should be readily appreciated that server 114 may be any number of computer servers which may communicate with each other over a distributed communication architecture.

Figure 2:
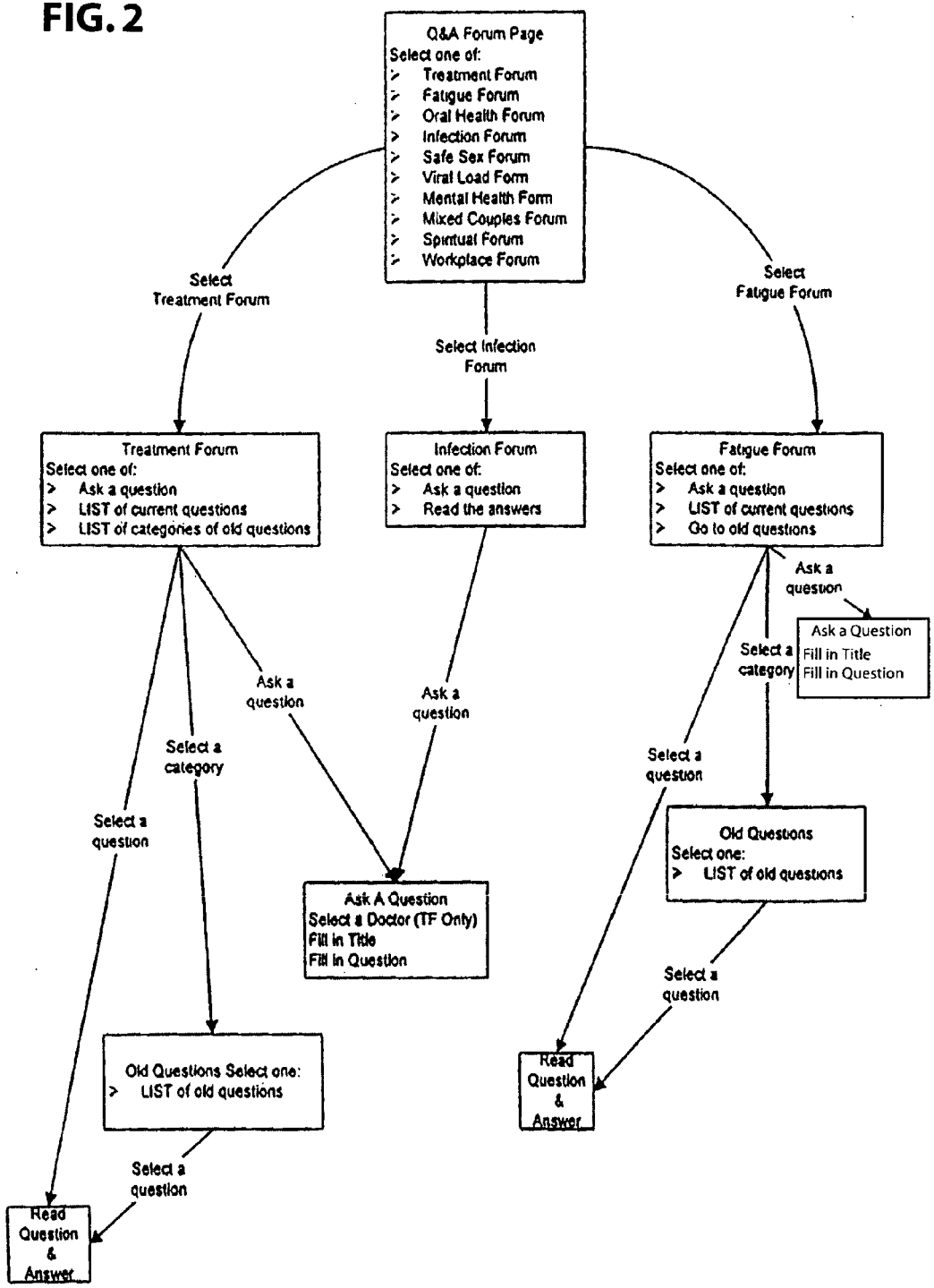
FIG. 2 is a flow chart of a user interface for a system consistent with the present invention.

FIG. 2 is a flow chart of one embodiment of a user interface for a system consistent with the present invention. Server 114 presents to the user a series of web pages. In response, the user makes selections via a client interface, e.g., computer 102, which are received by server 114. As shown in FIG. 2, the user is presented with a question-and-answer (Q&A) forum page, which offers a choice of fora, including: treatment, fatigue, oral health, infections, safe sex, viral load, mental health, mixed couples, spiritual, and workplace. Once the user selects a forum, a forum page presents the user with several options, including ask a question, select a question, and select a category. If the user chooses to ask a question, a new page prompts the user to enter a title, a question, and in some fora, an expert. If the user chooses to select a category, the user views a list of questions and chooses which questions to read. In response to the user selecting an archived question, the question and its associated answer are presented to the user.

FIG. 3 is an exemplary Q&A forum page that includes a header, sponsorship information, photos of experts, and a set of options corresponding to the available fora.

FIG. 4 is an exemplary forum page for the treatment forum as it appears at the user interface. The forum page lists the experts available in a specific forum. Experts can be available in one or more fora simultaneously. This allows users to address a panel of experts or have more private interaction with a single expert. The forum page presents the user with options such as reading a previously answered question or adding a new question. These options can be unique to each forum. If the user chooses to read previously answered questions, server 114 can list the questions or prompt the user to specify a category of questions to list. If the user chooses to ask a question, server 114 displays a page which prompts the user to fill in a question and title. In one embodiment, fora permit a user to select an expert to receive the question.

Figure 5:
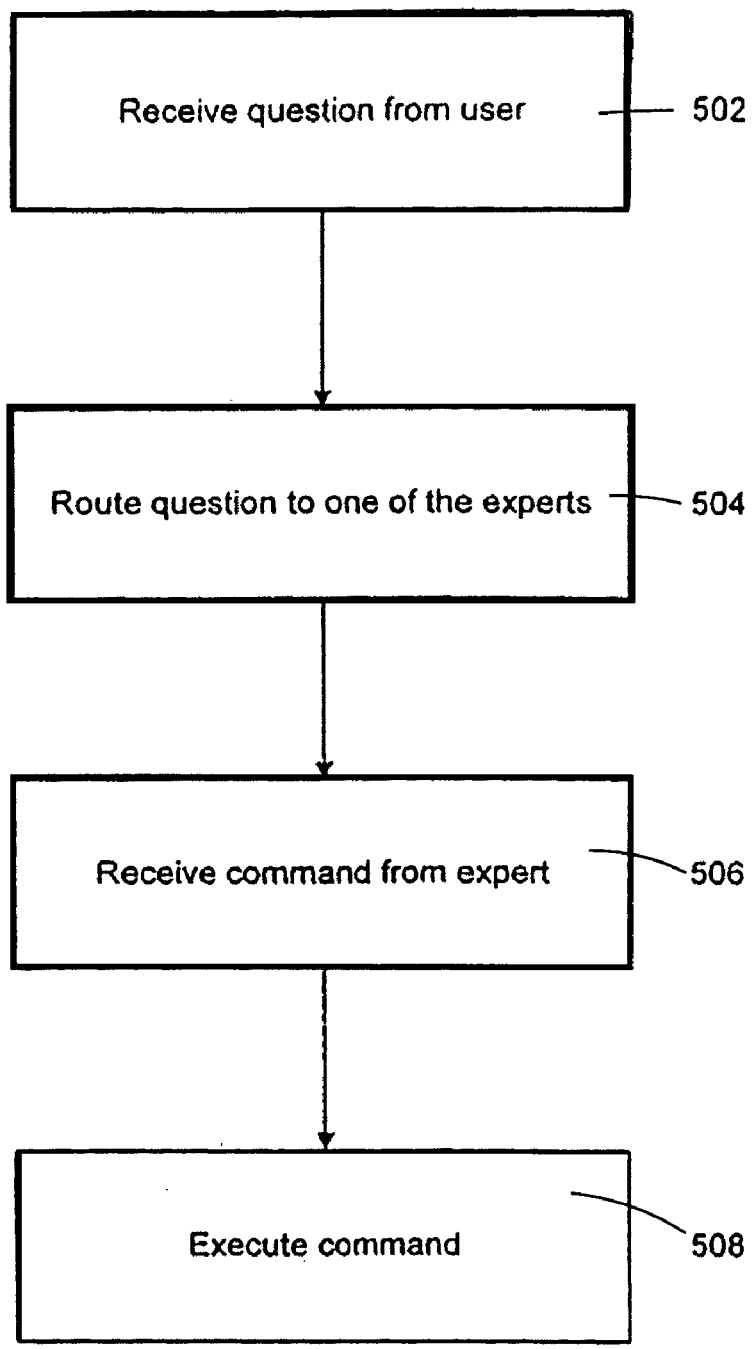
FIG. 5 is a flow chart depicting the steps involved with an expert's interaction with the system.

FIG. 5 is a flow chart depicting the steps involved with an expert's interaction with the system. The interaction begins when the system receives a question from the user (step 502). The question is input by the user at a client interface, such as computer 102, and transmitted via network 116 to server 114. Questions received by server 114 are filtered either automatically (e.g., using a computer or microprocessor) or by a human operator, such as a doctor, an expert, a medical professional, an insurance case manager and/or an administrator, to eliminate non-relevant or redundant questions. The system then routes the question to one of the experts (step 504) at an expert interface, such as computer 110. The system then receives a command from the expert (step 506) via the expert interface. Finally, the system executes the command (step 508) at server 114. Questions and/or answers are placed into one or more fora and/or categories either automatically (e.g., using a computer or microprocessor) or by a human operator, such as a doctor, an expert, a medical professional, an insurance case manager and/or an administrator.

Figure 6A:
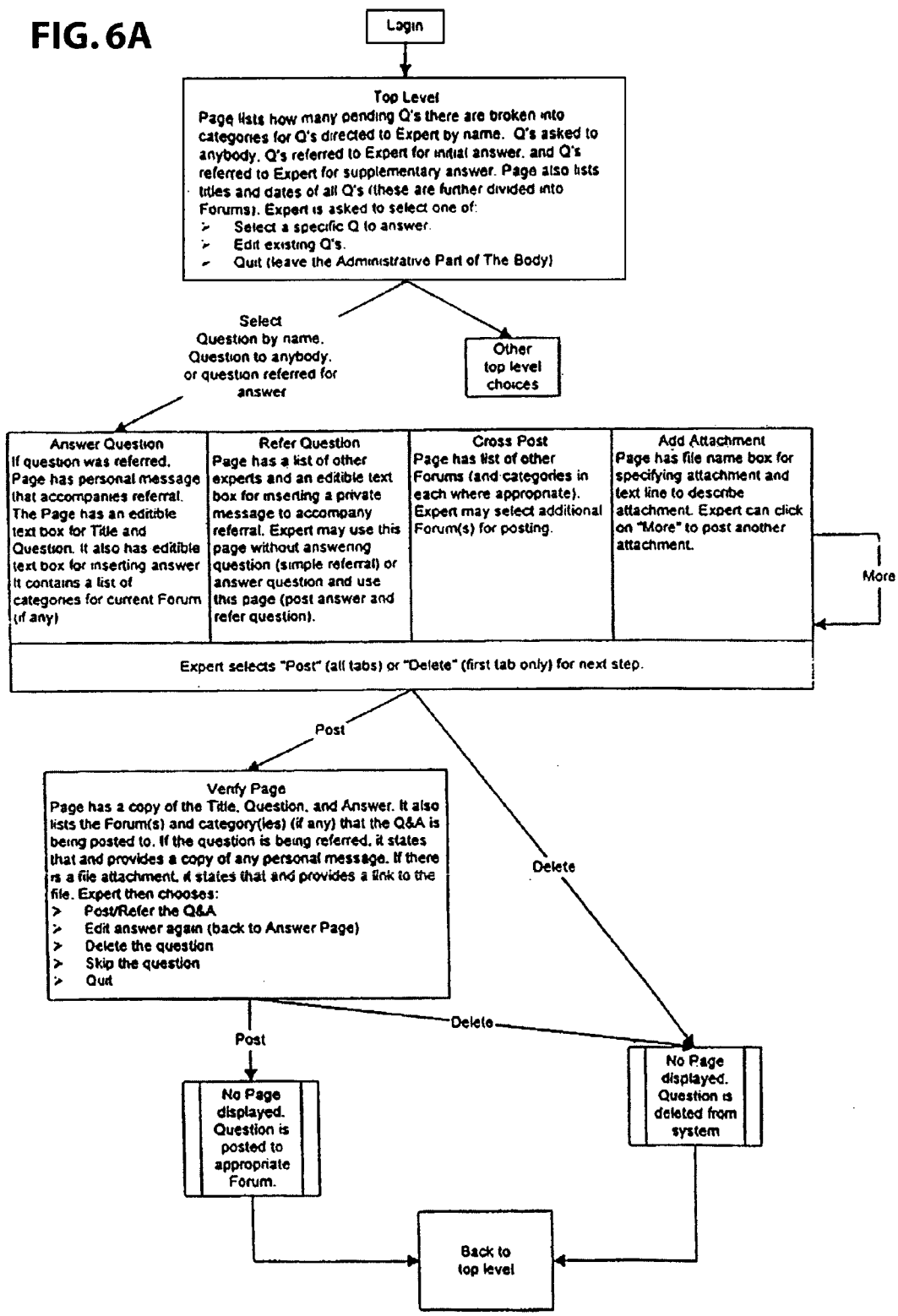
Figure 6C:
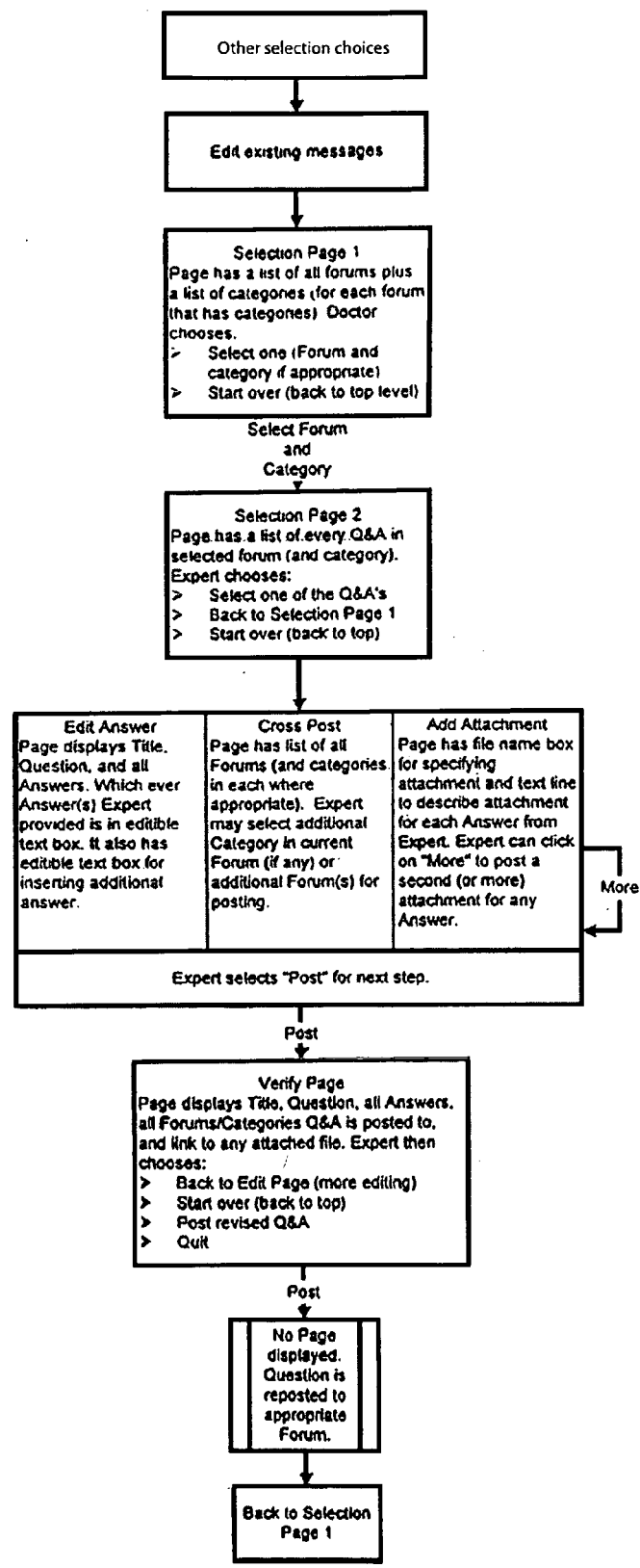

FIGS. 6A through 6C depict a flow chart showing one implementation of an expert's interaction in detail. The expert is presented with a home page, labeled "Top Level" in FIGS. 6A-C, from which they can select a specific question to answer, edit existing questions, or quit. As shown in FIGS. 6A and 6B, once the expert selects a question to answer, the expert can then answer the question, refer the question, cross post the question in other fora, or add an attachment. Upon completing the chosen tasks, the expert chooses either post or delete, and is returned to the top level home page. The post command prompts the expert to verify the results and then the question is posted to the appropriate forum. The delete command deletes the question from the system.

FIG. 6C shows that, to edit existing messages, the expert first chooses a forum (and category, if appropriate) and then chooses a question and answer to edit. The expert can then edit the answer, cross post the answer to other fora, or add an attachment. When finished, the expert selects the post command, which prompts the expert to verify the results and then the question is re-posted to the appropriate forum. The expert may then choose another forum or return to the top level home page.

FIG. 7 is an example of how an expert home page can appear on an expert interface, such as computer 110. It can include the expert's name, a summary of the questions awaiting the expert's attention, an edit option, and a quit option. As shown in FIG. 7, questions can reach an expert in one of four ways: (1) unanswered questions referred by another expert; (2) previously-answered questions referred by another expert; (3) questions directed to a specific expert by a user; and (4) questions posted by a user with no expert selected. Regardless of the origin of questions, they all appear on the expert's home page. Collating all of an expert's questions in this way saves time and effort previously spent by the expert visiting several different locations looking for questions.

Figure 8:
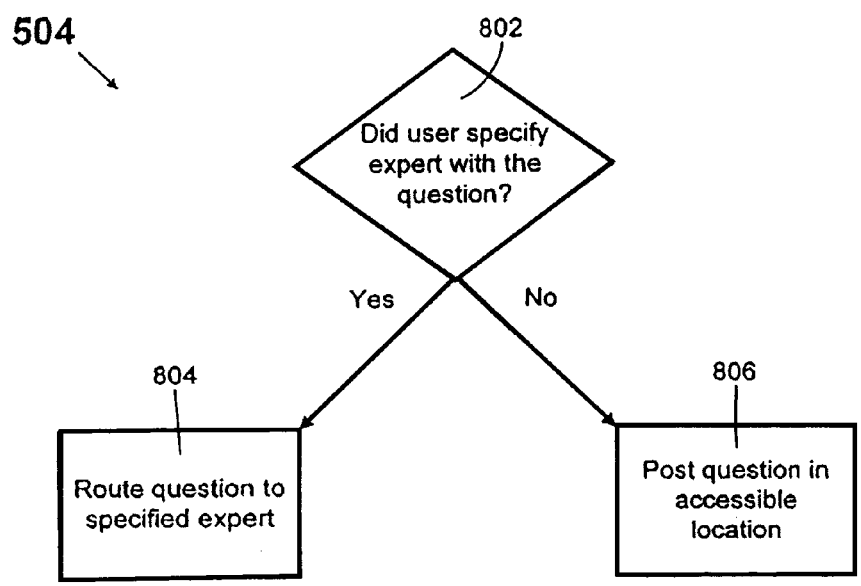
FIG. 8 represents the steps taken by the system to route a question to one of the experts.

FIG. 8 represents the steps taken by the system to route a question posed by a user to one of the experts (step 504). The system first determines whether the user specified an expert with the question (step 802). The user could have specified an expert while inputting the question at a client interface, such as computer 102. If the user specified an expert with the question, the system routes the question to that expert (step 804) at an expert interface, such as computer 110. If not, the system posts the question in a location on server 114 which is accessible to all experts in the forum (step 806).

Figure 9:
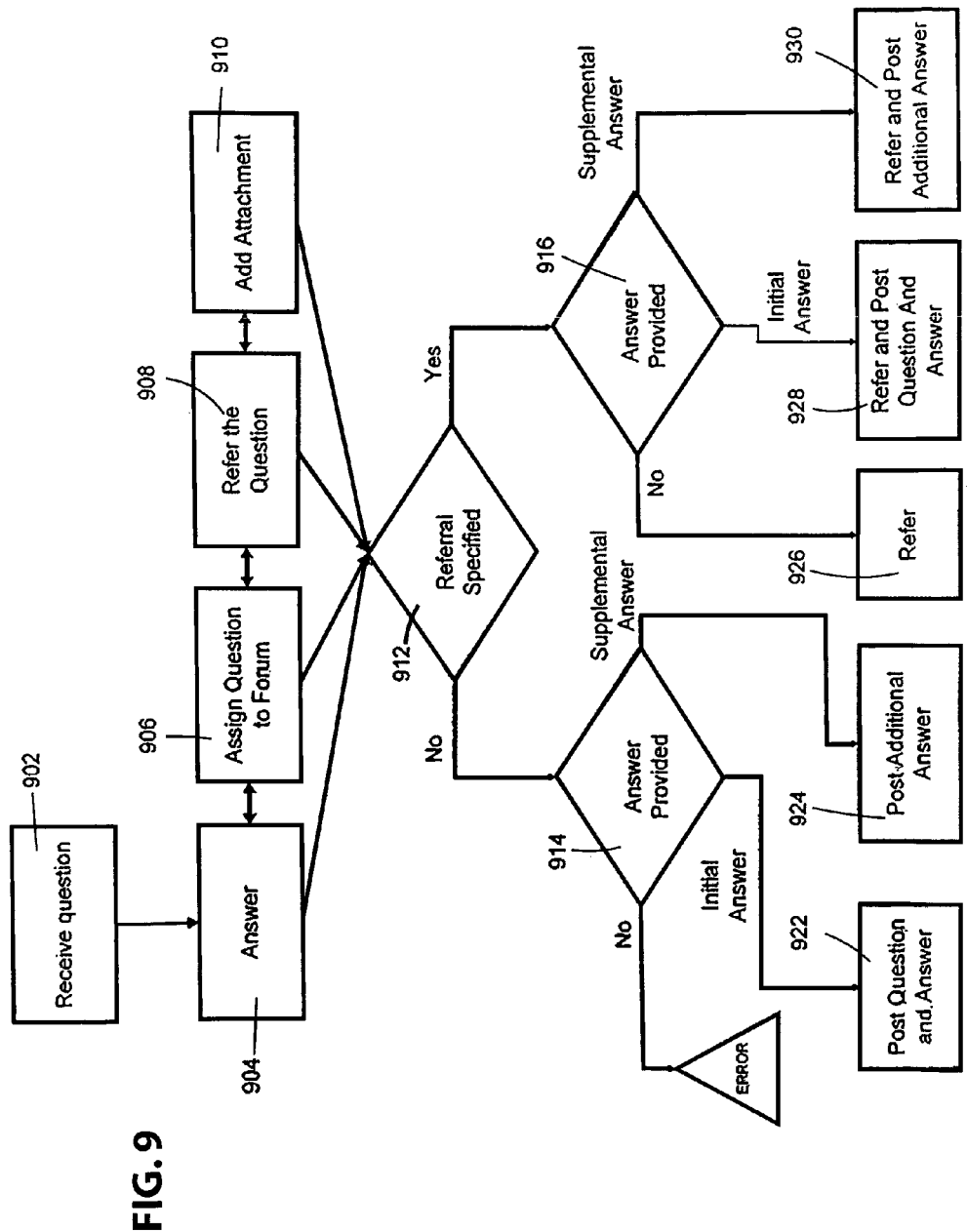
FIG. 9 is a flow chart illustrating options available to an expert upon receiving a question.

FIG. 9 is a flow chart illustrating options available to an expert upon receiving a question. First, the expert receives the question at an expert interface, such as computer 110 (step 902). The expert is presented with a four part answer set (steps 904, 906, 908 and 910) that allows him or her to make a variety of choices in answering the question. The expert can go from any part of the set to any other part at any time. In the first part, the expert can answer the questions (step 904); in the second part, he or she can assign the question to a forum and/or category (step 906); in the third part, he or she can refer the question to another expert (step 908); and in the last part, he or she can add an attachment to an answer to the question (step 910). Once the expert has completed the chosen task or tasks, he or she exits by specifying that the results be posted. The system then examines whether there was a referral or not (step 912) and whether there was any answer and, if so, whether it is the first one or a supplemental one (steps 914 and 916). Depending on what combination the system finds, it determines that it should do one of the following: simply post the question and answer (step 22), post a supplemental answer to an existing question (step 924), refer the unanswered question (step 926), post the question and answer and refer it for a supplemental answer (step 928), or post the supplemental answer and also refer it for another supplemental answer (step 930).

A benefit of this embodiment is that real-time peer review is provided to experts. Experts in many fields rely on review by their peers to validate their opinions and research. Medical journals provide one avenue of peer review, but the publishing process of medical journals can take months. Second opinions provide another avenue for peer review, and patients frequently get a second opinion before accepting the treatment prescribed by their doctor. But, getting a second opinion can take weeks, during which the patient has to postpone treatment. Real-time peer review may speed up treatment.

Experts, such as doctors, can post answers to questions and then refer their answers to peer review personnel, such as other doctors, insurance case managers and/or other experts for a second (or third or fourth, etc.) opinion. Peer review personnel can also review answers given by other experts on their own, without being asked to do so by an expert. Users, including patients, can request that specific experts answer a question and then the users can read comments from other experts on those answers. Using the present invention, this entire review process can occur within hours, or even minutes.

FIG. 10 shows the interaction, consistent with the current invention, between a system and an administrator using administrator interface 112. First, an administrator logs into the system via administrator interface 112 (step 1002). The system then presents the administrator with a menu of guides stored on server 114 (step 1004). Each guide consists of a set of choices corresponding to different aspects of a forum within the system. After presenting a menu of guides to the administrator, the system receives a command from the administrator, via administrator interface 112, selecting a guide (step 1006). The system then presents the guide selected to the administrator at administrator interface 112 (step 1008). Next, the system receives an action command from the administrator, via administrator interface 112, in response to the guide (step 1010). The system then executes the command received (step 1012). The administrator can then choose, via administrator interface 112, to log out (step 1014), or be presented with the menu of guides again, returning to step 1004.

FIG. 11A through 11J depict a flow chart showing one implementation of an administrator's interaction in detail. The administrator is presented with a home page, labeled "Top Level", which offers several options, including: configure the system, add or configure a forum, configure an expert, add or delete an administrator, edit a question or answer, correct a forum manually, view new material, or change the administrator's password.

Figure 11A:
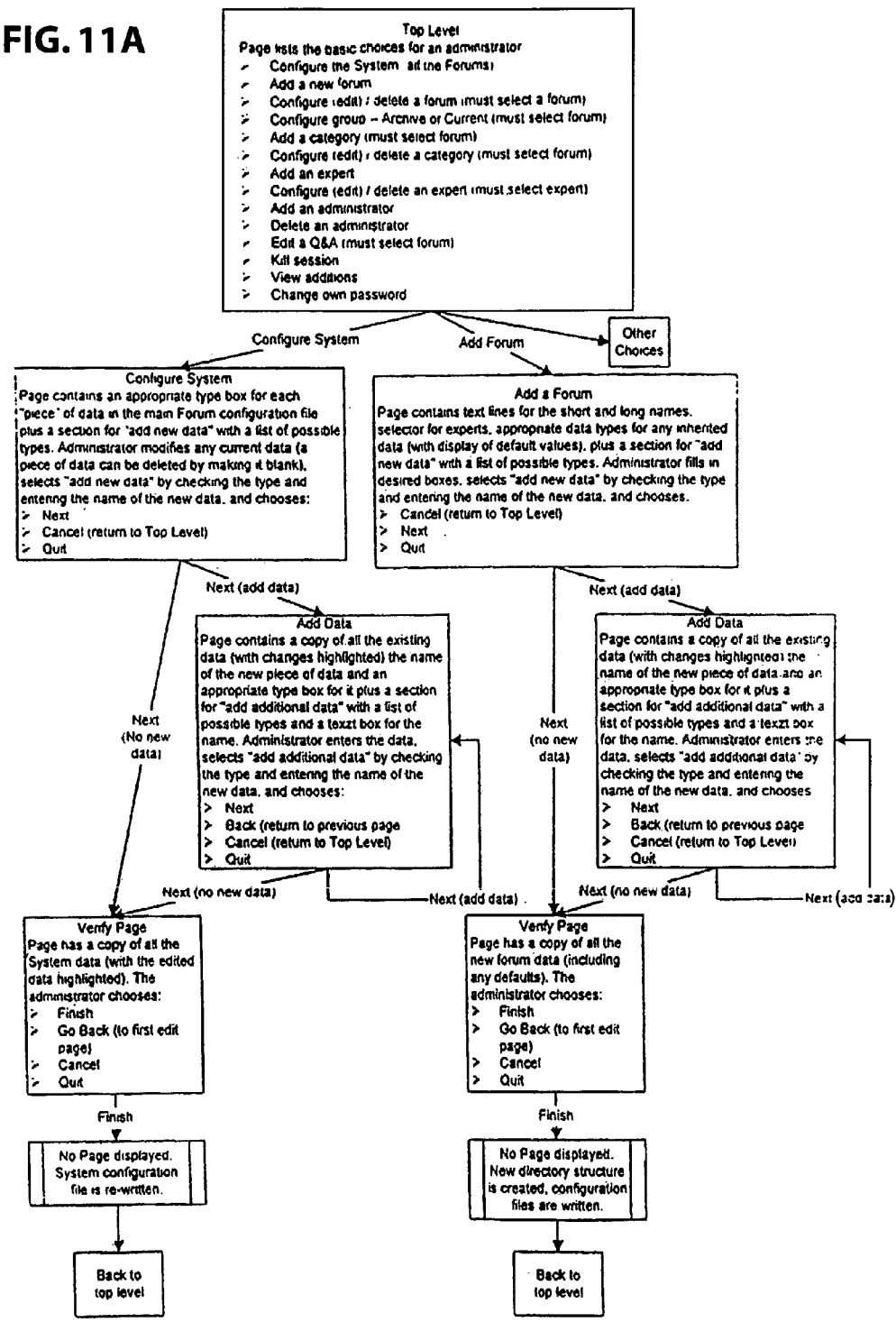
FIGS. 11A-J depict a flow chart showing one implementation of the administrator's interaction in detail.

As FIG. 11A shows, when the administrator chooses to configure the system, a configure system page is presented which contains information for the system configuration files and requests new data. The administrator can choose next (to add data), cancel (to return to the home page), or quit (to exit). The page for adding data contains a copy of existing data and the new data. From the add data page, the administrator can choose next, back (return to previous page), cancel (return to home page), or quit (exit). If "next" is selected, or if no new data is being added, the administrator is prompted to verify the page, after which the finish command makes the appropriate changes and presents the home page.

As shown in FIG. 11A, the process is the same for adding a forum as for configuring the system, except that instead of a configure system page, an add forum page is presented which contains forum names, expert selectors, data types and requests new data.

Figure 11B:
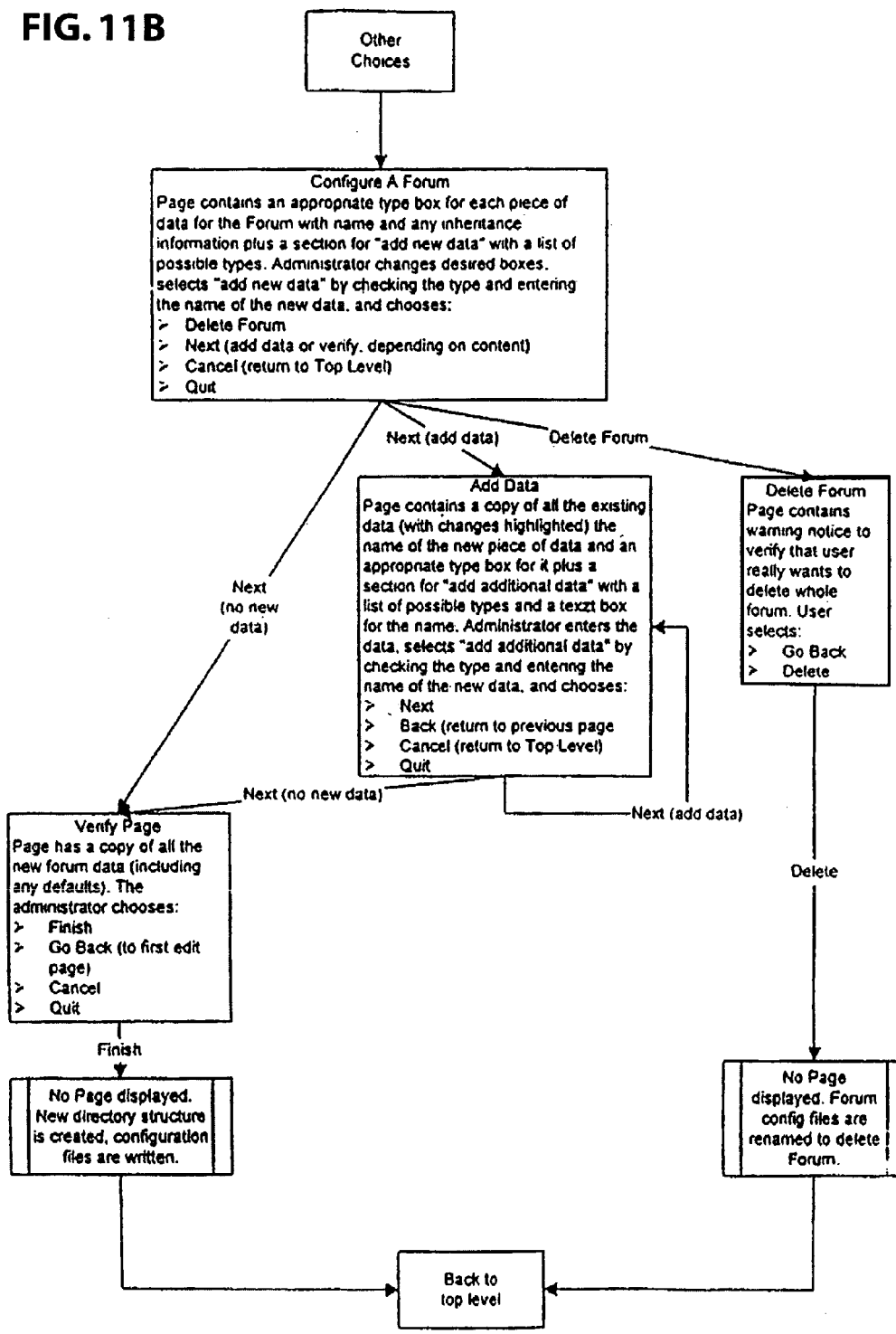

As shown in FIG. 11B, the process is the same for configuring a forum as for configuring the system, except that instead of a configure system page, a configure forum page is presented which contains the forum name and inheritance information, and requests new data. Also, from the configure forum page the administrator can choose to delete a forum, which prompts the user to verify the selection and then deletes the forum from the system.

Figure 11C:
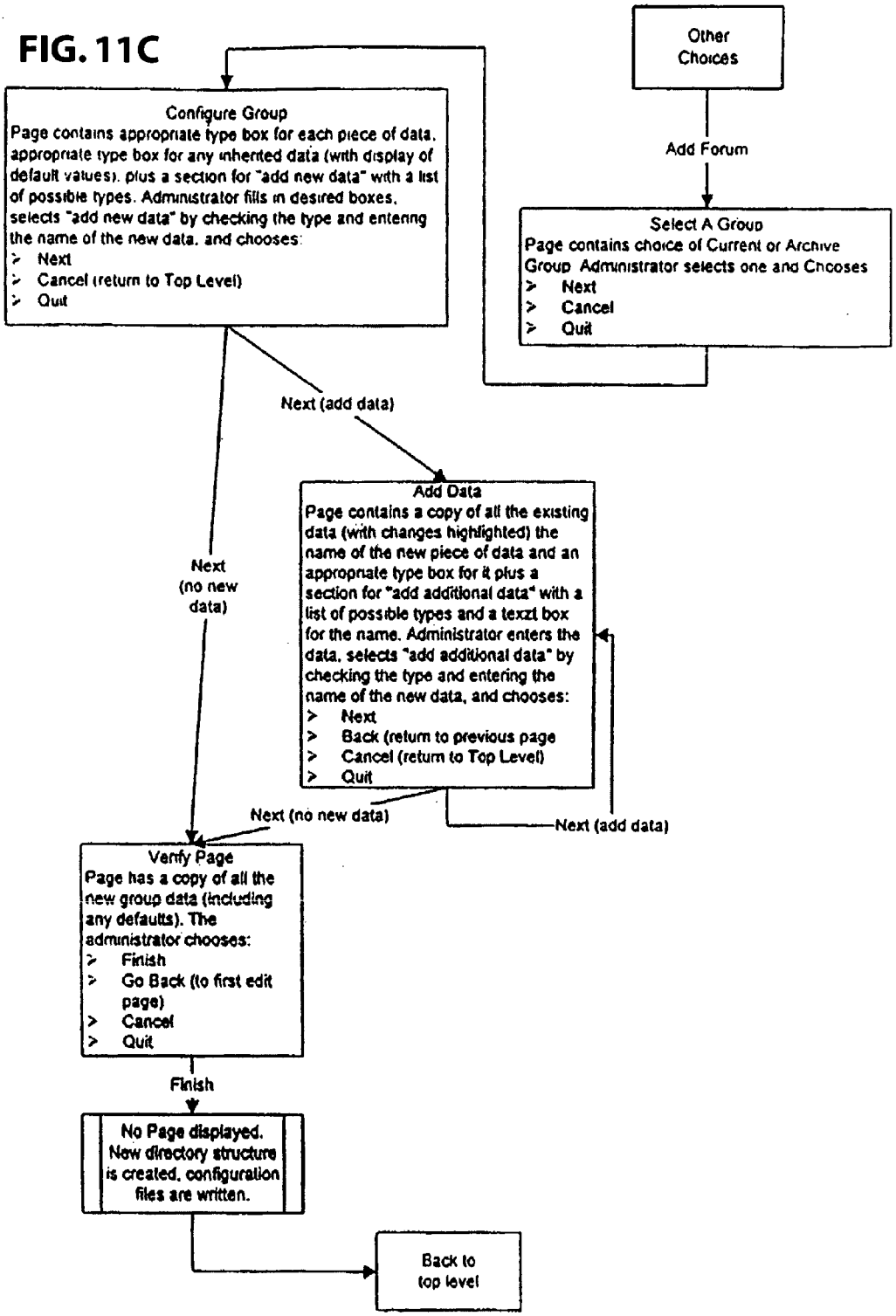

As shown in FIG. 11C, the process is the same for configuring a group as for configuring the system, except that instead of a configure system page, the administrator first selects a group and then a configure group is presented which contains the group data and requests new data.

Figure 11D:
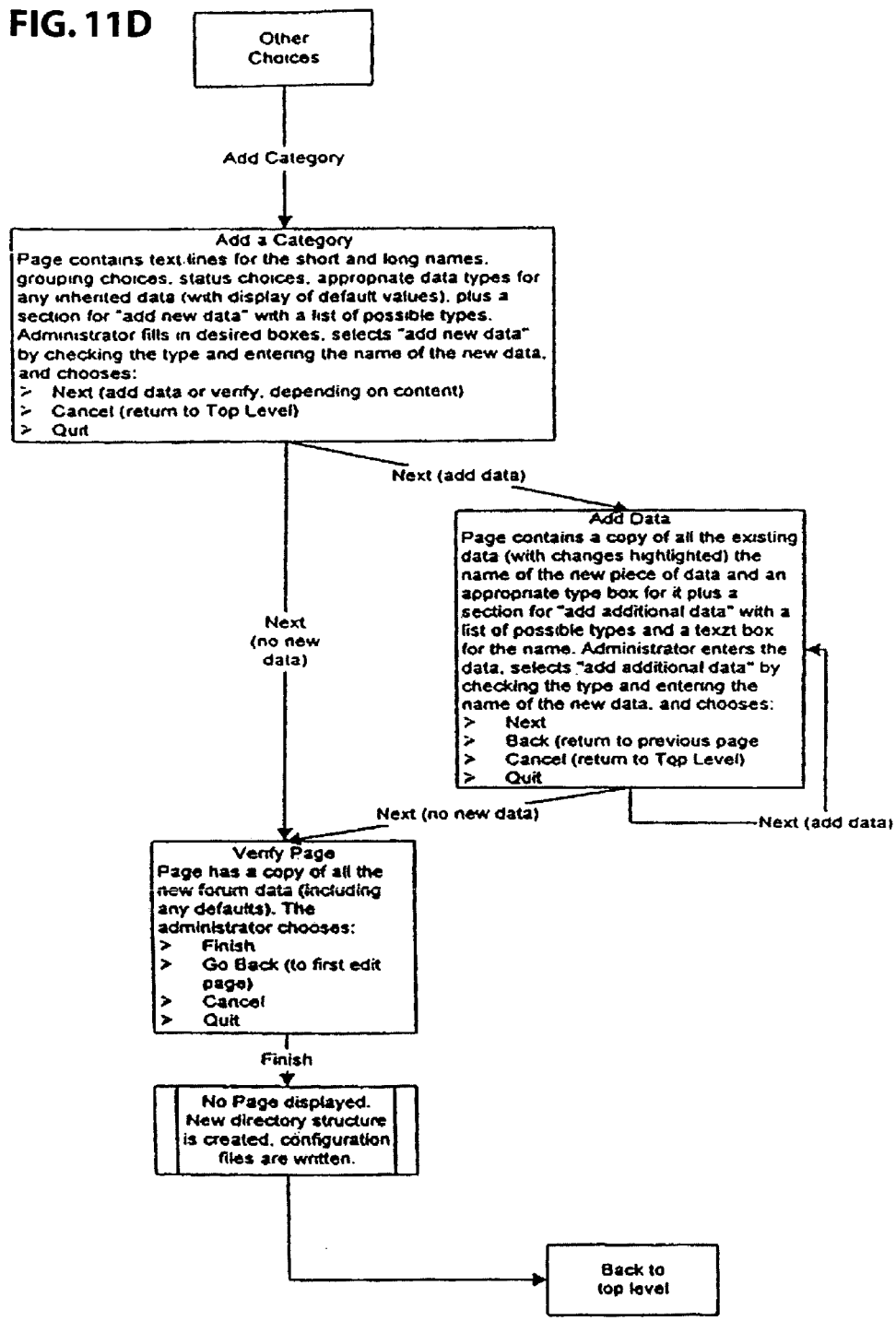

As shown in FIG. 11D, the process is the same for adding a category as for configuring the system, except that instead of a configure system page, an add category page is presented which contains category names, grouping choices, status choices, inheritance information, and requests new data.

Figure 11E:
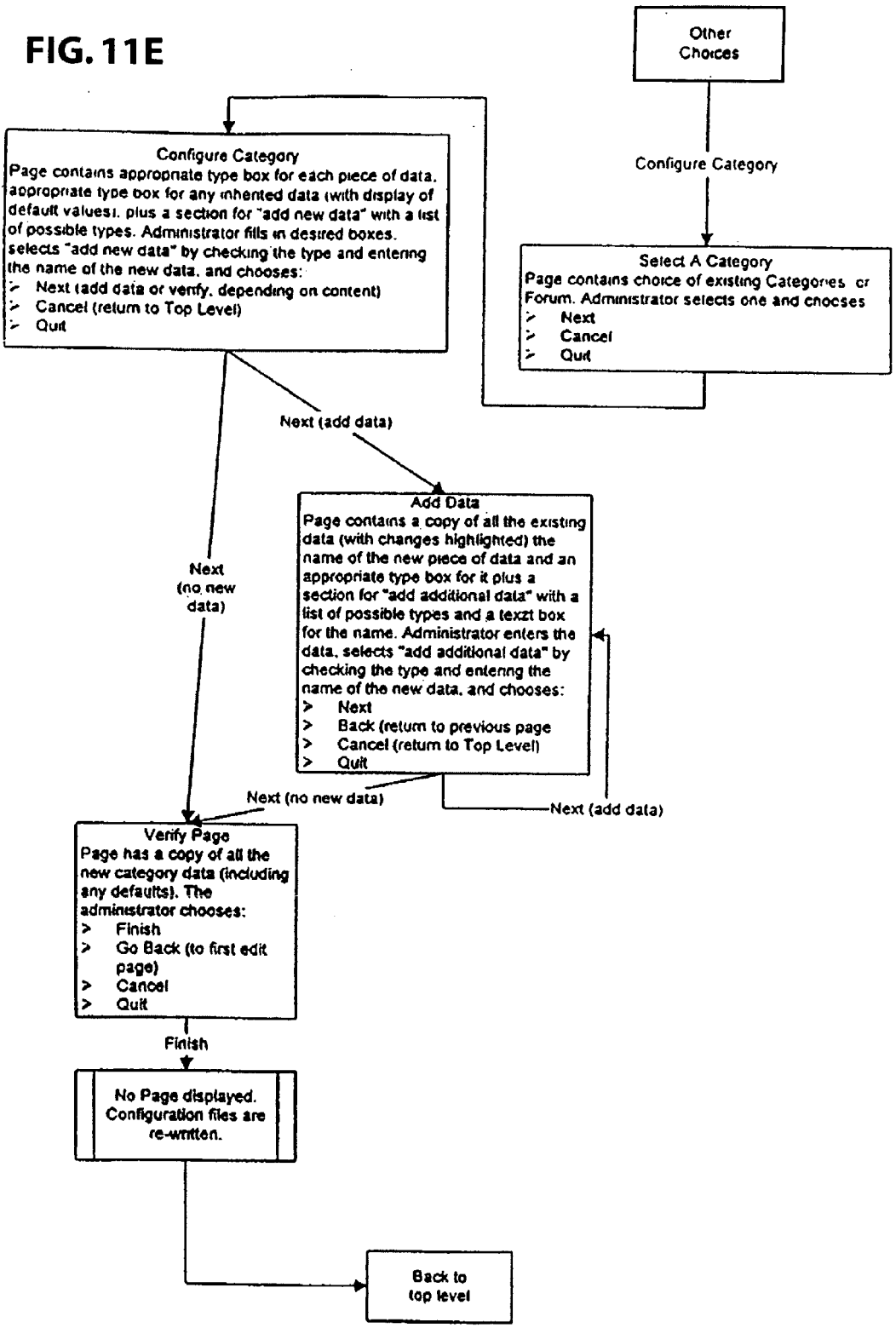

As shown in FIG. 11E, the process is the same for configuring a category as for configuring the system, except that instead of a configure system page, the administrator first selects a category and then a configure category page is presented which contains category data and requests new data.

Figure 11F:
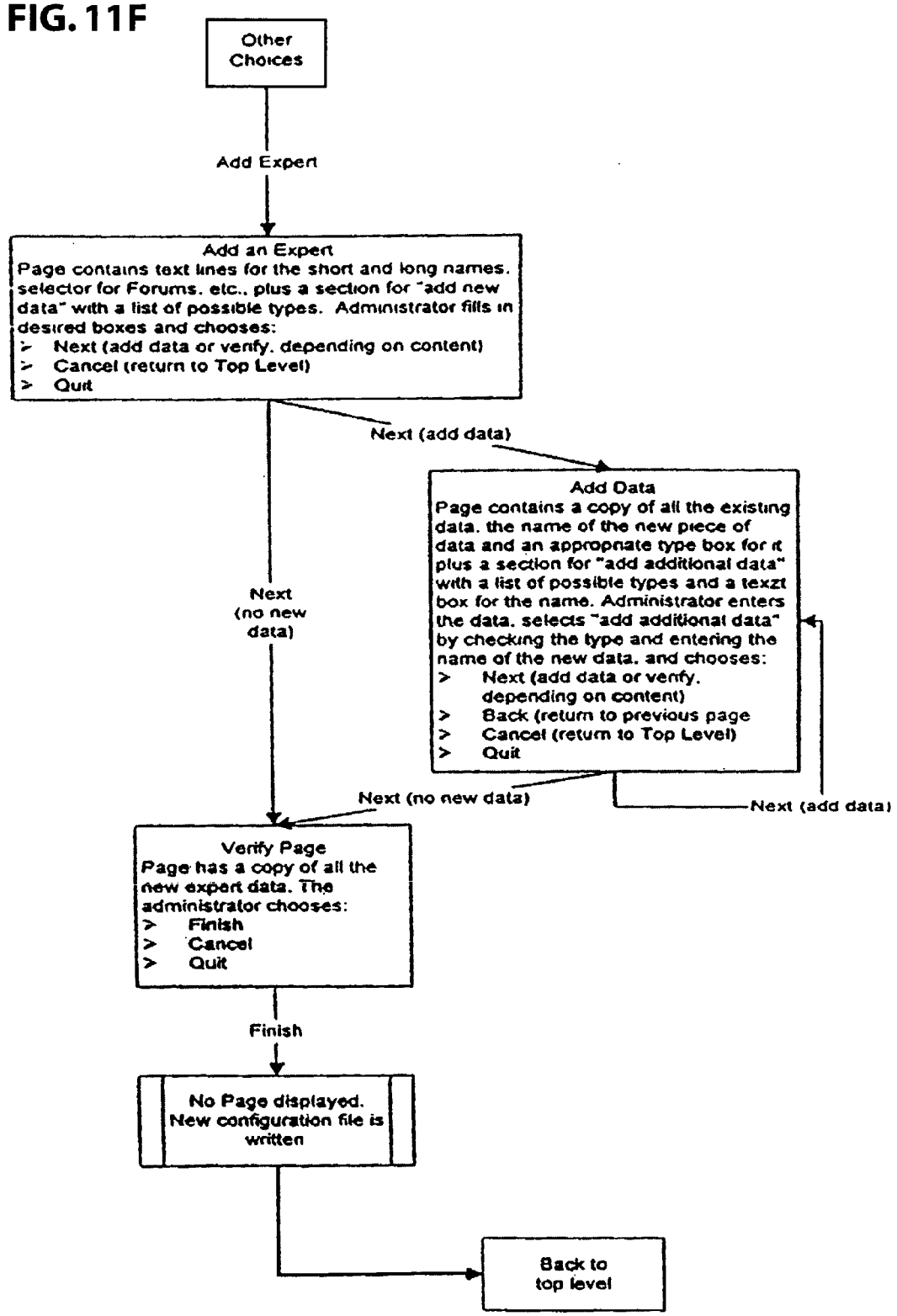

As shown in FIG. 11F, the process is the same for adding an expert as for configuring the system, except that instead of a configure system page, an add expert page is presented which requests expert names, forum selection, and any new data.

Figure 11G:
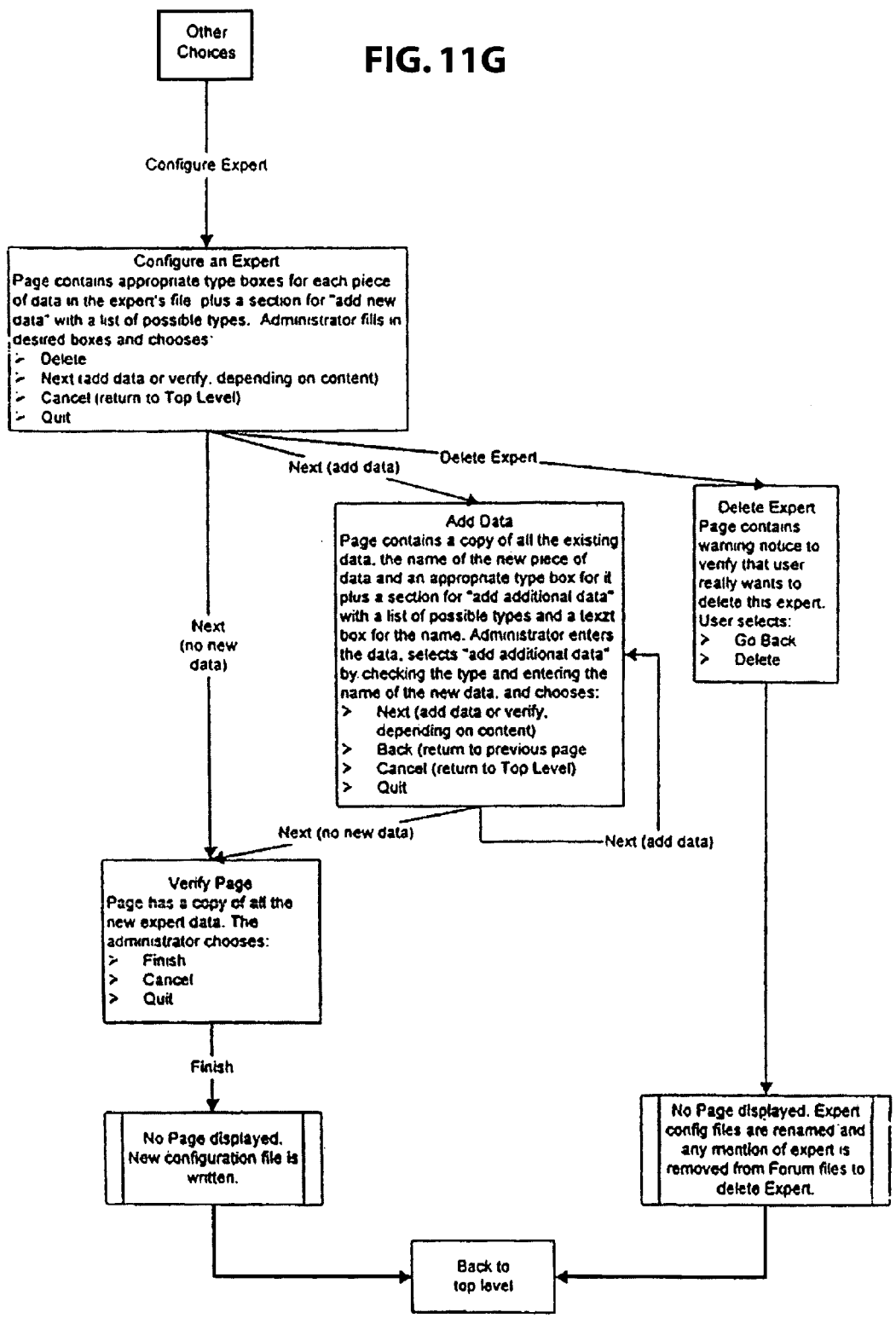

As shown in FIG. 11G, the process is the same for configuring an expert as for configuring the system, except that instead of a configure system page, a configure expert page is presented which contains the expert data and requests any new data. Also, from the configure expert page, the administrator can choose to delete an expert, which prompts the user to verify the selection and then deletes the expert from the system.

Figure 11H:
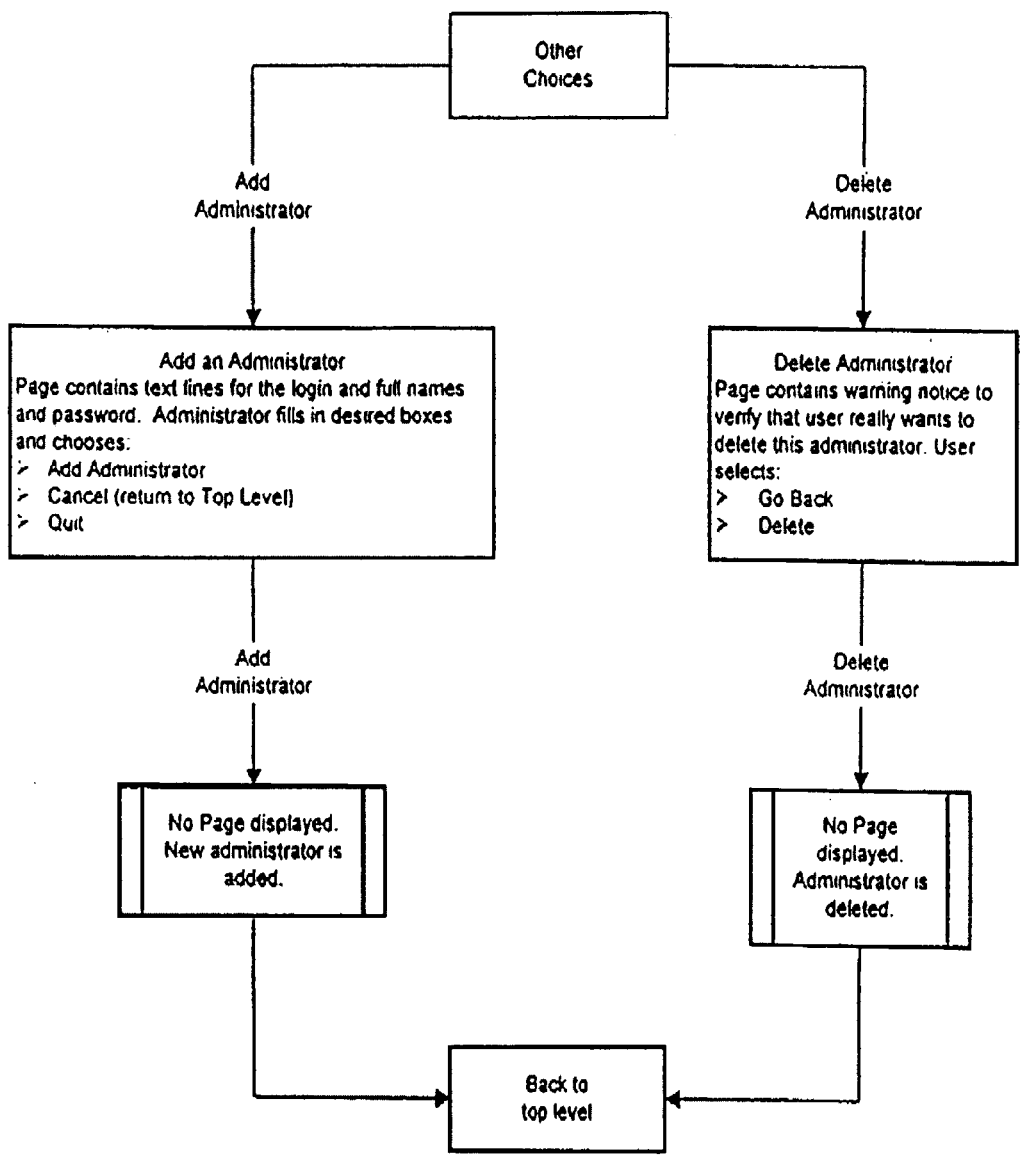

As shown in FIG. 11H, if the administrator chooses to add an administrator, an add administrator page is presented, which requests long and short names and a password. From that page, the administrator can choose add (adds the new administrator and returns to the home page), cancel (returns to the home page), or quit (exit).

As shown in FIG. 11G, if the administrator chooses to delete an administrator, a delete administrator page is presented, which prompts the administrator to verify the delete command or return to the home page. Once the command is verified, the administrator to be deleted is removed from the system, and the administrator returns to the home page.

Figure 11I:
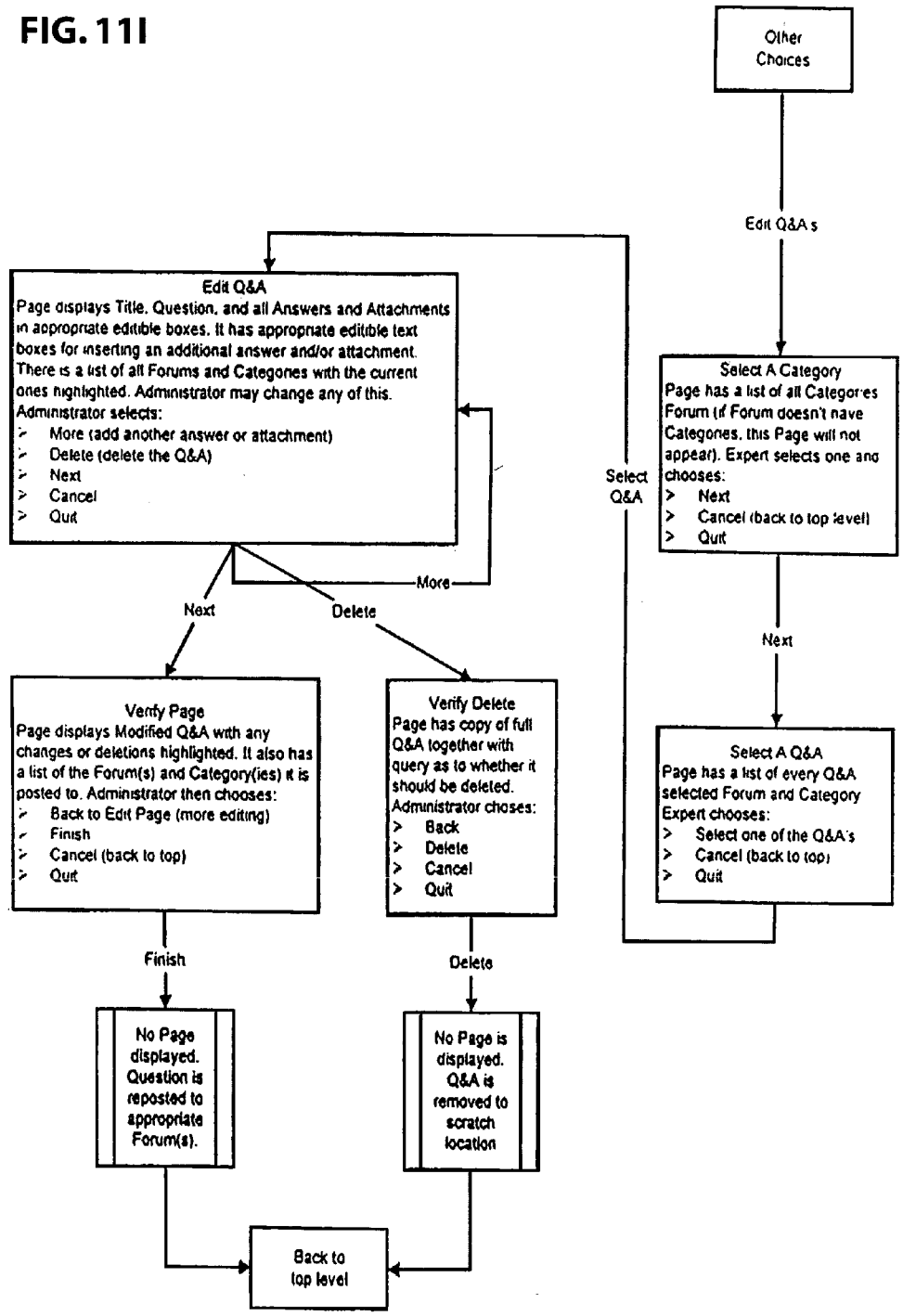

As shown in FIG. 11I, if the administrator chooses to edit a question and answer, the administrator then chooses a category and a question and answer. An edit question and answer page is presented which displays the title, question, all answers and attachments, and all relevant forums and categories. The administrator can change the information or delete the question and answer. To change the information, the administrator is prompted to verify and post the question and answer. To delete, the administrator must verify the command and then the question and answer is deleted. After deleting a question and answer, or after verifying a question and answer, the administrator returns to the home page.

Figure 11J:
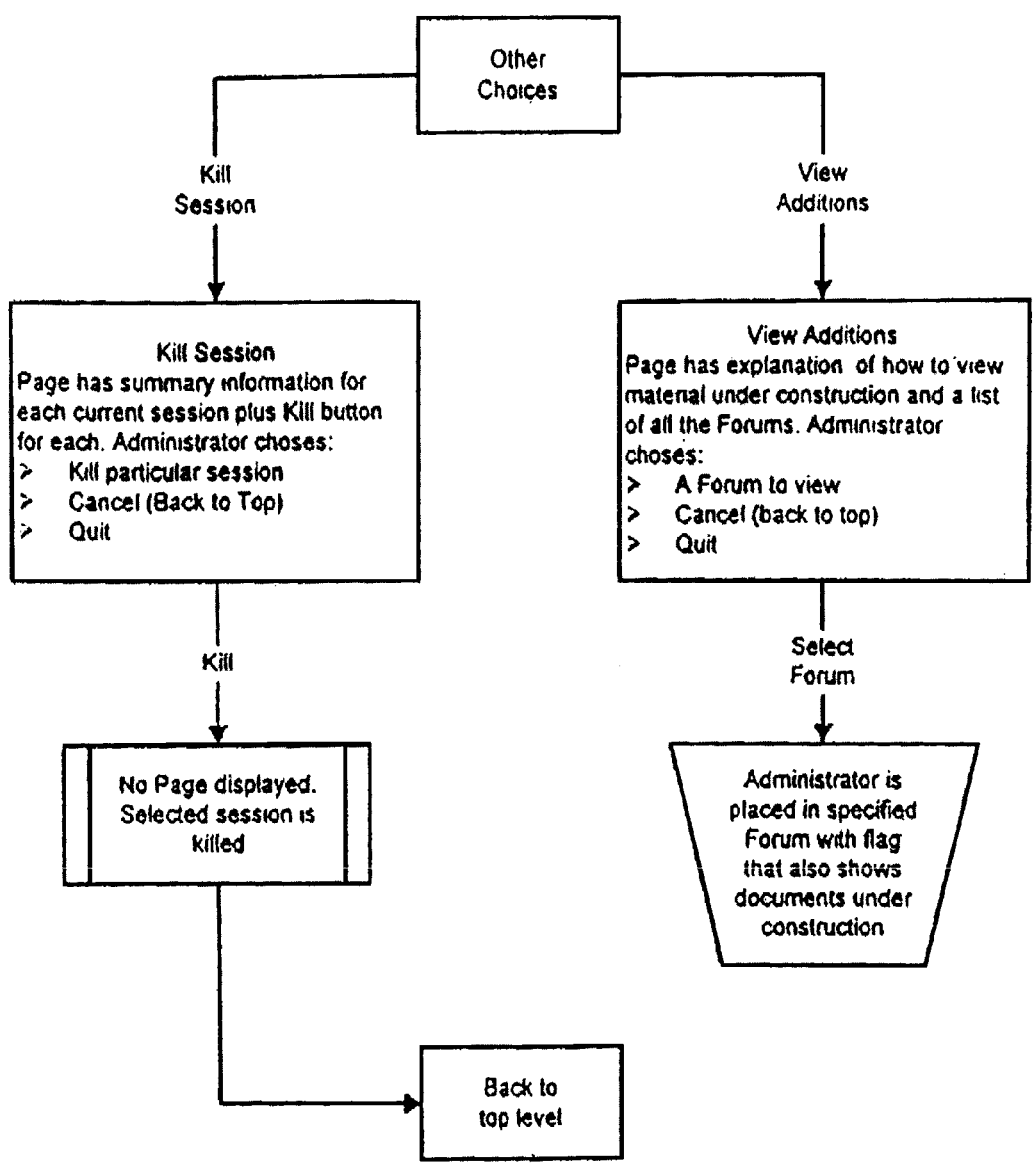

As shown in FIG. 11J, if the administrator chooses to kill a session, a kill session page is presented which has summary information for each current session and a kill button for each. The administrator can choose to kill a session, to cancel (return to the home page), or to quit (exit). If the kill option is selected, the session is killed and the administrator returns to the home page.

FIG. 11J also shows that, if an administrator chooses to view additions, a view additions page is presented which has a list of all forums. The administrator selects a forum to view and is presented with that forum which contains flags that show documents under construction.

FIG. 12 is an example of how an administrator's home page can appear on an administrator's interface, such as computer 112. The home page can include the administrator's name as well as the options available to the administrator, including a quit option.

Figure 13:
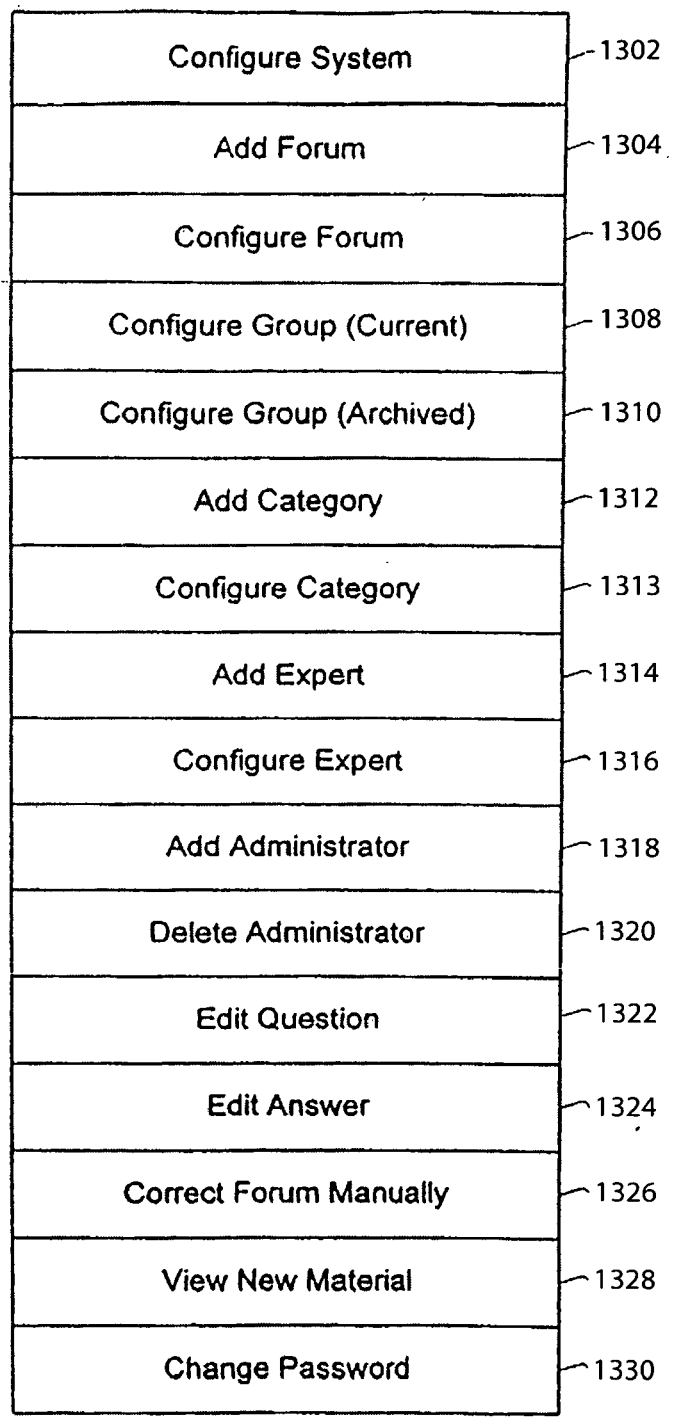
FIG. 13 represents the menu of guides which are stored on a server and presented by the system to an administrator.

FIG. 13 represents the menu of guides, stored on server 114, presented by the system to the administrator via administrator interface 112 in step 1004. The administrator can choose to configure the system (step 1302), add a forum (step 1304) or configure a forum (step 1306), configure a group of either current (step 1308) or archived (step 1310) messages, add (step 1312) or configure (step 1313) a category, add an expert (step 1314) or configure an existing expert (step 1316). Guides are also available to allow the administrator to add an administrator (step 1318) or delete an administrator (step 1320). The administrator has the capacity to edit a question (step 1322) or edit an answer (step 1324). The administrator also has the option to correct a forum manually (step 1326). Finally, the administrator can select the guide to view new material being added to the site (step 1328) or to change that administrator's password (step 1330).

Figure 14A:
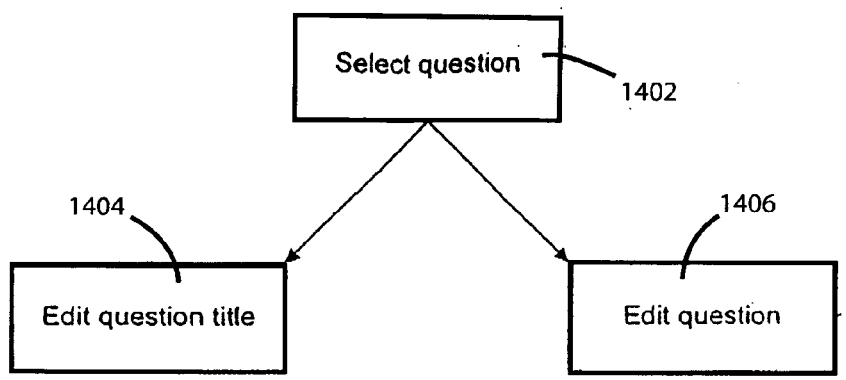
FIGS. 14A-B illustrate an administrator's ability to edit questions and answers for content or for other reasons.
Figure 14B:
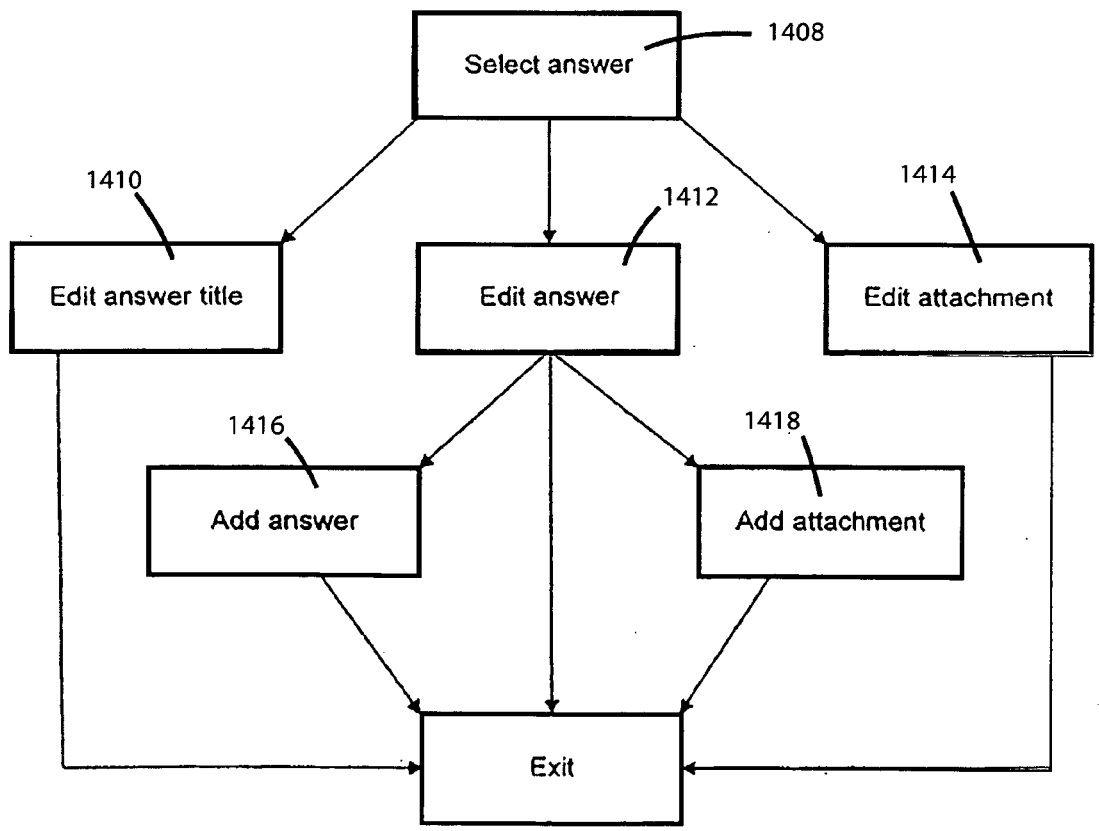

FIGS. 14A and 14B depict an administrator's ability to edit questions and answers content or for other reasons. The administrator, using administrator interface 112, can either select a question (step 1402) or select an answer (step 1408). If the administrator selects a question (step 1402), the administrator can then choose one of two options via administrator interface 112: (1) edit the question's title (step 1404), or (2) edit the question itself (step 1406). If the administrator selects an answer (step 1408), the administrator can use administrator interface 112 to choose from several options. The administrator can edit the title of an answer (step 1410). The administrator can also choose to edit the answer itself (step 1412). In editing an answer (step 1412), the administrator can choose to add an answer (step 1416) or add an attachment to that answer (step 1418). The administrator can also choose to edit an attachment to an existing answer (step 1414).

Systems consistent with the present invention can interact with users, experts, and administrators through presenting a series of web pages. Web pages are made up of a number of fields. To display a web page, server 114 must locate the correct data for each field in the web page. Each field has a "name", e.g., <HEADING>, and a "value", e.g., <Answers to Treatment Questions>. The names of corresponding values are arranged in (name, value) pairs and stored in configuration files (e.g., system.cfg).

One way in which the current system may maintain these configuration files is using a hierarchical configuration of levels. Each level may be a collection of configuration files corresponding to a part of the system. To display a web page, the system searches the configuration files at each level. The information found at the lowest level may be displayed. This allows the administrator to specify default settings at the highest level while customizing any part of the site by changing the (name, value) pairs at the corresponding level.

Figure 15:
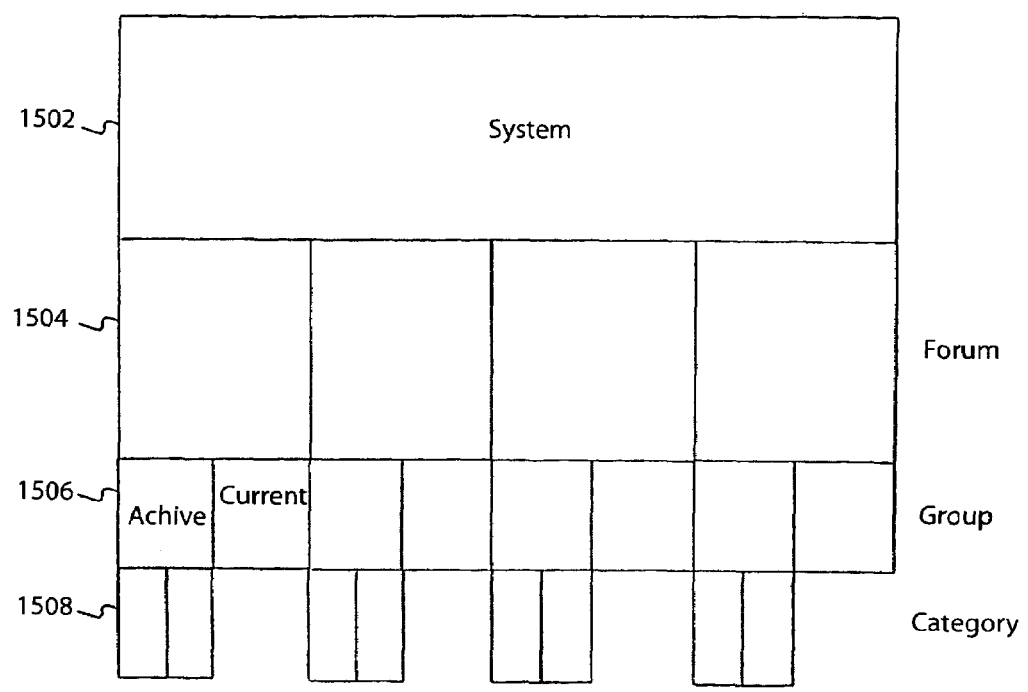
FIG. 15 is a high-level system diagram of a hierarchical configuration of levels, one way in which the current system can be implemented.

FIG. 15 is a high-level system diagram of one such hierarchy. The levels are arranged in order of increasing generalization. The highest level of generalization is the system level 1502. At a lower level of generalization than the system level is the forum level 1504. At a lower level of generalization than the forum level is the group level 1506. The groups at level 1506 can be either current or archived. At a lower level of generalization than the archived groups is the category level 1508. It is also possible to have a separate expert level.

When the system is searching for the heading text to be displayed at the top of a page currently in the prevention category of the treatment forum, the system starts at the top (system.cfg) and looks for a <HEADING> block. The system then visits each configuration file on the way down the hierarchy (forum.cfg would next in this example). Preferably, the system would use the matching <HEADING> block it finds at the lowest level.

Figure 16:
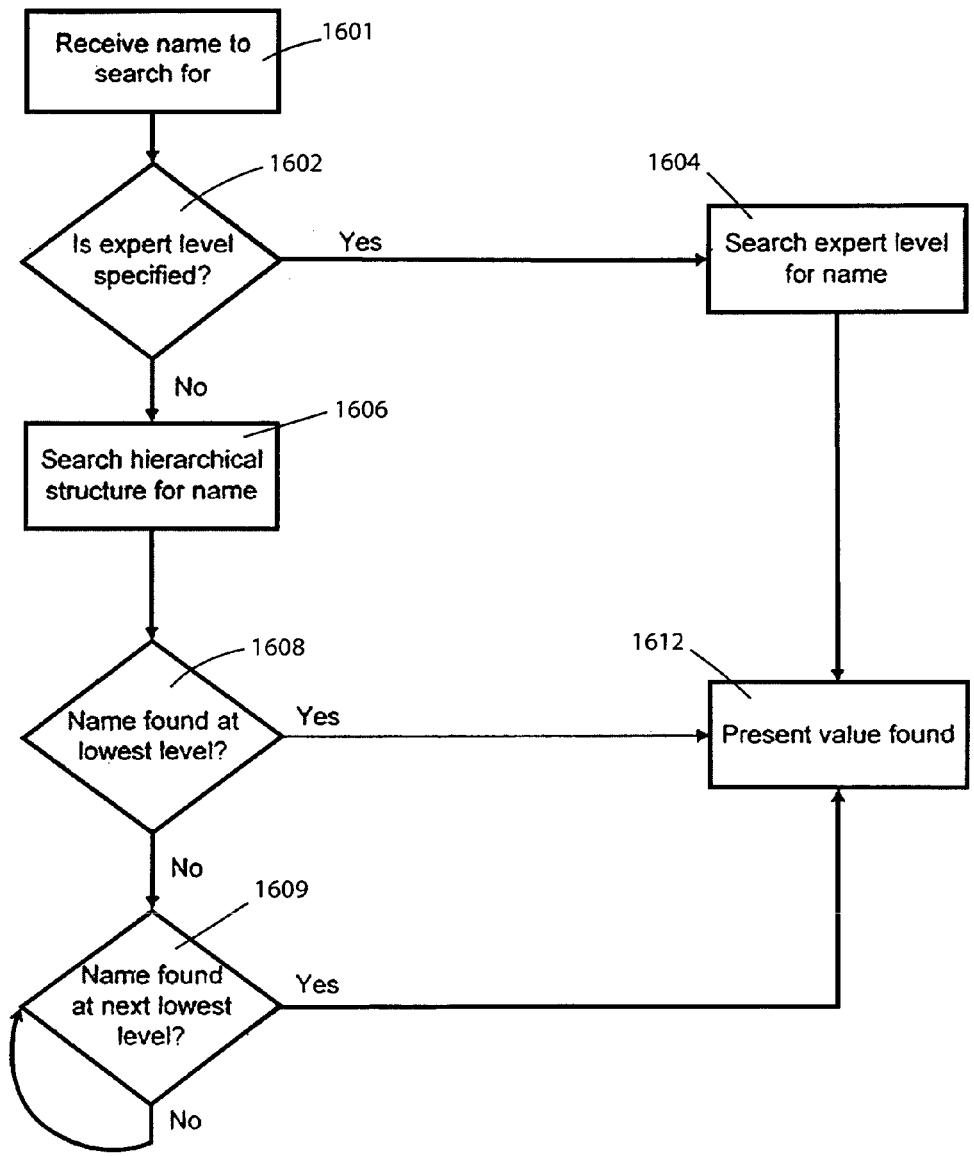
FIG. 16 is a flow chart showing the steps for displaying the proper web page information.

FIG. 16 is a flow chart showing the steps for displaying the proper web page information. First, the system receives the name to search for (step 1601). If the expert level is specified along with the name (step 1602), the system searches for the value corresponding to the given name at the expert level of the server (step 1604). The system then returns at the level (step 1612). If the expert level is not specified, the system searches for the name and its corresponding value (step 1606). Beginning at the lowest level of generalization (step 1608), the system searches iteratively, moving to the next lowest level of generalization (step 1609) until the name is found. The system then presents the value corresponding to that name (step 1612).

If the levels are arranged in a hierarchical fashion, the administrator can change or create new pages at a certain level of the system by changing the value in the correct configuration file at the level. In addition, configuration files can correspond to each expert in the system, making it possible for the administrator to maintain settings for all experts for each expert individually.

Although preferred methods for searching, generating and presenting web page information have been presented in the foregoing, it will be readily apparent to one of ordinary skill in the art that other methods may likewise be used without departing from the spirit and scope of the present invention.

Figure 17:
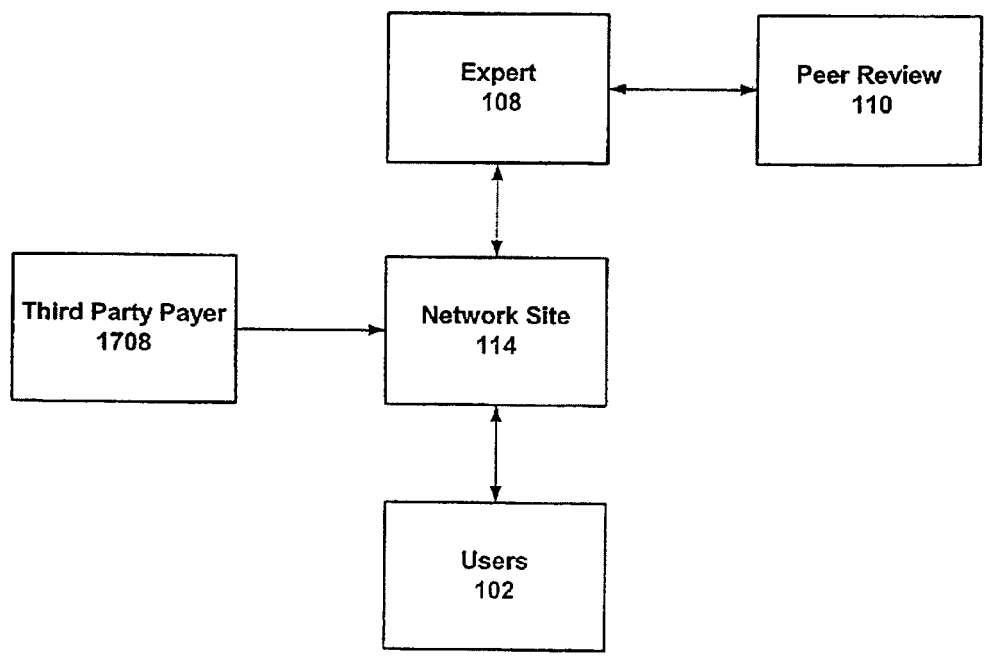
FIG. 17 is a schematic block diagram illustrating a further embodiment of the information-sharing system of FIG. 1.

Referring now to FIG. 17, therein is depicted one preferred embodiment of the present invention. Methods for funding the network site 114 will be described in conjunction therewith.

In one embodiment, the network site 114 may provide a plurality of fora dedicated to one or more topics of interest to the public, for example, providing expert opinions on one or more medical topics as described above. One or more users 102 may interact with the network site 114 over the network 116 by submitting questions to one or more of the provided fora, and receiving responses thereto from one or more experts 108. The answers may be reviewed by peer review personnel 110, prior to or after the posting of the expert's answer to the user's question. In addition, the questions and responses may be posted to one or more fora with appropriate topic headings so that other users may access and review questions and answers of interest.

In a particular embodiment, users 102 may be members of the public who may access the fora provided by network site 114 over the Internet in order to receive medical advice pertaining to a medical condition, receive second opinions on medical treatment they are receiving, and the like. Such users 102 may be provided access to the network site 114 free of charge or they may be required to pay a fee to access the site. The fee may be charged on a per transaction basis, or may be a subscription fee to access the site for a predetermined amount of time, e.g. one month or one year. Further, the fee may be paid on behalf of a user or a group of users by a third party, such as a health plan to which the user or the group belongs or a vendor whose products may be sold to the user or the group. The fees may be collected by an operator of the network site 114 in any known manner, such as receiving credit card information from the users 102, or verifying that the fee has been paid, for example, by a third party payer 1708.

In place of fees, banner advertisements and the like may be placed on various pages presented by the network site 114 for viewing by the users 102. In such case, site traffic may be monitored in order to receive appropriate advertisement fees from the third parties 1708 who placed the banner advertisements.

Alternatively, in lieu of fees, the user may be required to submit personal information, such as demographic information, user identification information, user financial information, medical treatment information and the like, to the network site 114. Such information may be useful to the owner of the network site 114 and/or the third party provider 1708 in that the information could be used to attain advertising revenue or to build a database of potential customers based on the submitted information. Accordingly, upon the provision of such information, any fees that may be charged to access the network site 114 may be waived.

It is further contemplated that a user 102 may receive points for each submission they make to the network site 114. The points would be tracked and awarded in a manner similar to frequent flier miles, as is well known in the art. A user 102 may receive discounts on health premiums, may have access fees waived or paid for by a third party, or receive a preferred status with health care providers or insurers based on point accumulation. Alternatively, points may be issued to a user for reasons not associated with the network site. These points, in turn, may be redeemed by the user for accessing the network site. By way of example, a pharmacy may issue points to its customers based on their purchases at the physical location. Thereafter, the points may be redeemed by the customers for accessing a Q & A network site related to medical and drug topics.

In a further embodiment, the users 102 may be doctors or other medical personnel who wish to receive continuing medical education credits for accessing medical education fora that may be provided by the network site 114. Such users 102 may be provided with educational instruction in return for payment of a fee in any manner described above.

In another embodiment of the present invention, third party payers 1708, such as medical insurance providers, health maintenance organizations (HMOs), drug companies, and any other party with an interest in the subject matter of the plurality of fora offered, may provide funding to the site or may advertise their services on the site through banner advertisements. In one preferred embodiment, the third party payer 1708 may provide an unrestricted educational grant to the operator of the network site 114 in exchange for the provision of medical fora to members of the public related to particular topics, such as medical treatments, medical conditions, and the use of drugs for the same. Such grants may be of the type governed and regulated by the U.S. Food and Drug Administration. In exchange for third party funding, the operator of the network site 114 may provide site traffic information to the third party payer 1708 in order to confirm that medical information is being disseminated to the public in an efficient manner. A third party payer 1708, such as an HMO, may participate in this embodiment in order to improve the quality of care of health care being received by participants and/or to reduce health costs related to a user 102 through reviewing medical or drug treatment information provided by the expert 100 and/or the user 102.

The network site 114 may also provide users 102 with a set of questions to be answered. The questions are intended to elicit how much understanding a user 102 has of a subject forum. From these submissions of answers, a report on user comprehension may be prepared and provided to third party payer 1708 in exchange for the funding. The identity of users 102 who submit responses may be omitted from such a report in order to preserve the privacy and confidentiality of each user 102. The answers to such questions may also be used to monitor the appropriateness or the outcomes of an expert's advice provided to the user 102 through the plurality of fora on the network site 114.

Experts 108 may be one or more doctors or other medical professionals who specialize in particular medical fields of interest. Peer review 110 is provided by peer review personnel, such as other doctors, other experts, administrators, insurance case managers, or other medical professionals. Experts 108 and peer review personnel may be compensated by the operator of the network site 114 in any known manner.

In one particular embodiment, it is contemplated that a third party payer 1708, such as an HMO, may operate the network site 114 as a private network. Users 102 may, in turn, be individuals who receive medical coverage from, or groups of individuals represented under a coverage plan provided by the third party payer 1708. The users 102 may be provided with user identifications and passwords to access the private network site 114. In this embodiment, the expert 108 may be a doctor who provides second opinions as to the medical treatment being received by the user and reported to the network site 114. Peer review 110 may be provided by HMO case managers and the like in order to monitor medical treatment and advice being received by the users 102. Alternatively, the users 102 may first provide medical treatment information and the like to insurance case managers, in lieu of the expert 108. The insurance case manager may then provide the medical information to an expert 108 for their second opinion.

The third party payer 1708 may, in turn, adjust medical insurance premiums or pay any access fees on behalf of the users 102 who receive second opinions from and report statuses of medical or drug treatments to the network site 114. In the case where medical insurance premium adjustments are provided, the third party payer 1708 may increase a premium for a user 102 in order to subsidize the operation of the site. Alternatively, the third party payer 1708 may decrease the premium in order to encourage use of the network site 114. As described above, use of the network site 114 may lower health costs incurred by the user 102 since the third party payer 1708 may review and approve medical and/or drug treatments being received by the user 102.

Figure 18:
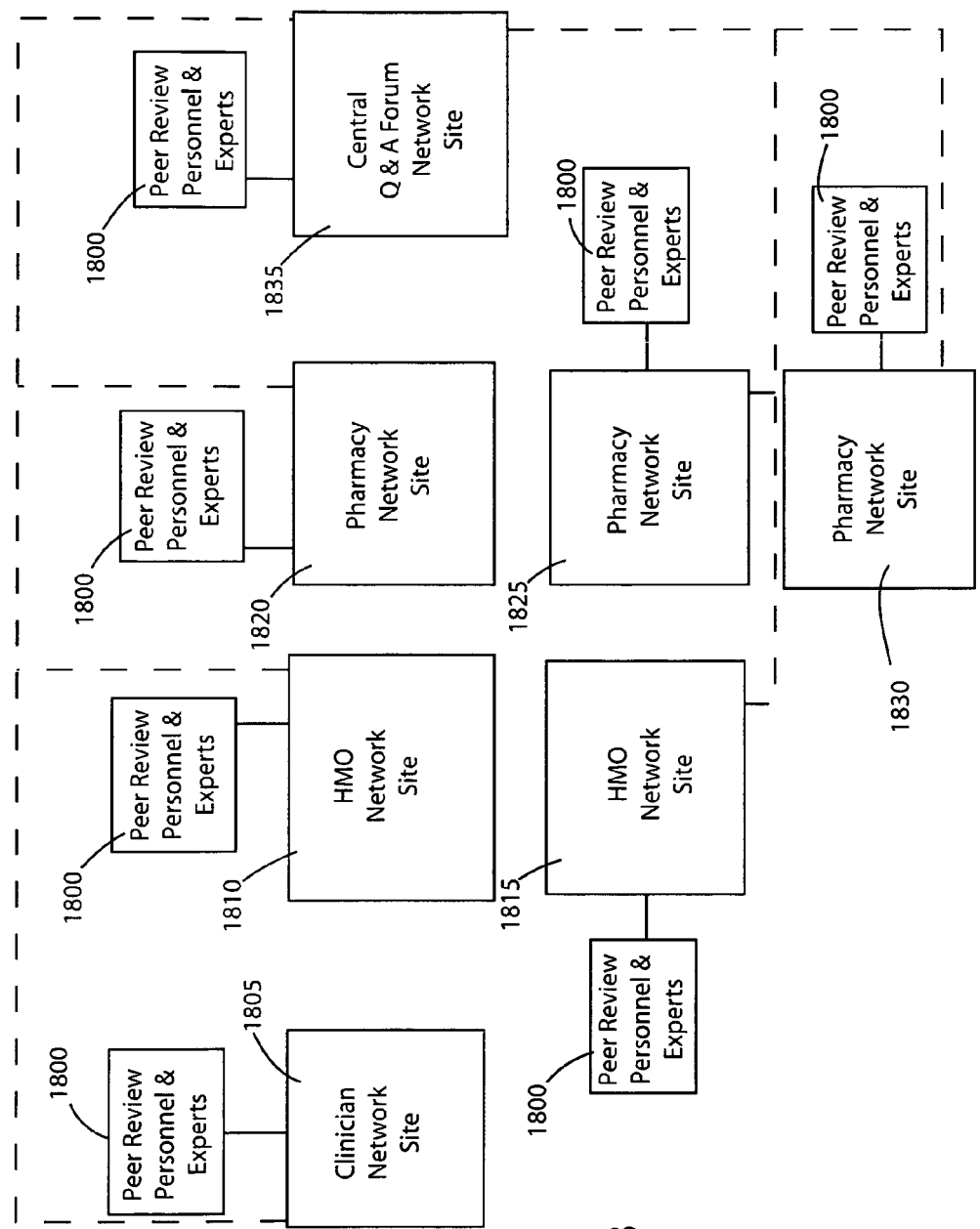
FIG. 18 is an exemplary block diagram of the question and answer forum installed at multiple network sites with a global sharing of experts and peer review personnel for responding to questions asked by users at any of the network sites.

The system for managing questions and answers may be deployed at one or more network sites. As described above, the user may access a network site in order to view previously answered questions or to generate their own question. One of the advantageous features of the system in accordance with the present invention is the ability for the system to be deployed or installed at more than one network site. FIG. 18 is an exemplary embodiment in which the system is installed at four different categories or groupings of network sites including a generic question and answer forum network site 1835, a clinician network site 1805, two different health maintenance organization (HMO) operated network sites 1810, 1815, and three different pharmacy network sites 1820, 1825, 1830. Although four different categories or groupings of network sites are shown and described, it is within the intended scope of the invention for the system to be installed in any number and in different categories or groupings of network sites than those identified herein. Furthermore, the system may be deployed in any number of one or more network sites in each category or group of network sites. In the example shown in FIG. 18, the generic question and answer forum network site 1835 is accessible by any user, whereas the question and answer forum in the three other categories of network sites is limited to clinicians, members of a particular HMO, and members of a particular pharmacy, respectively.

Figure 19:
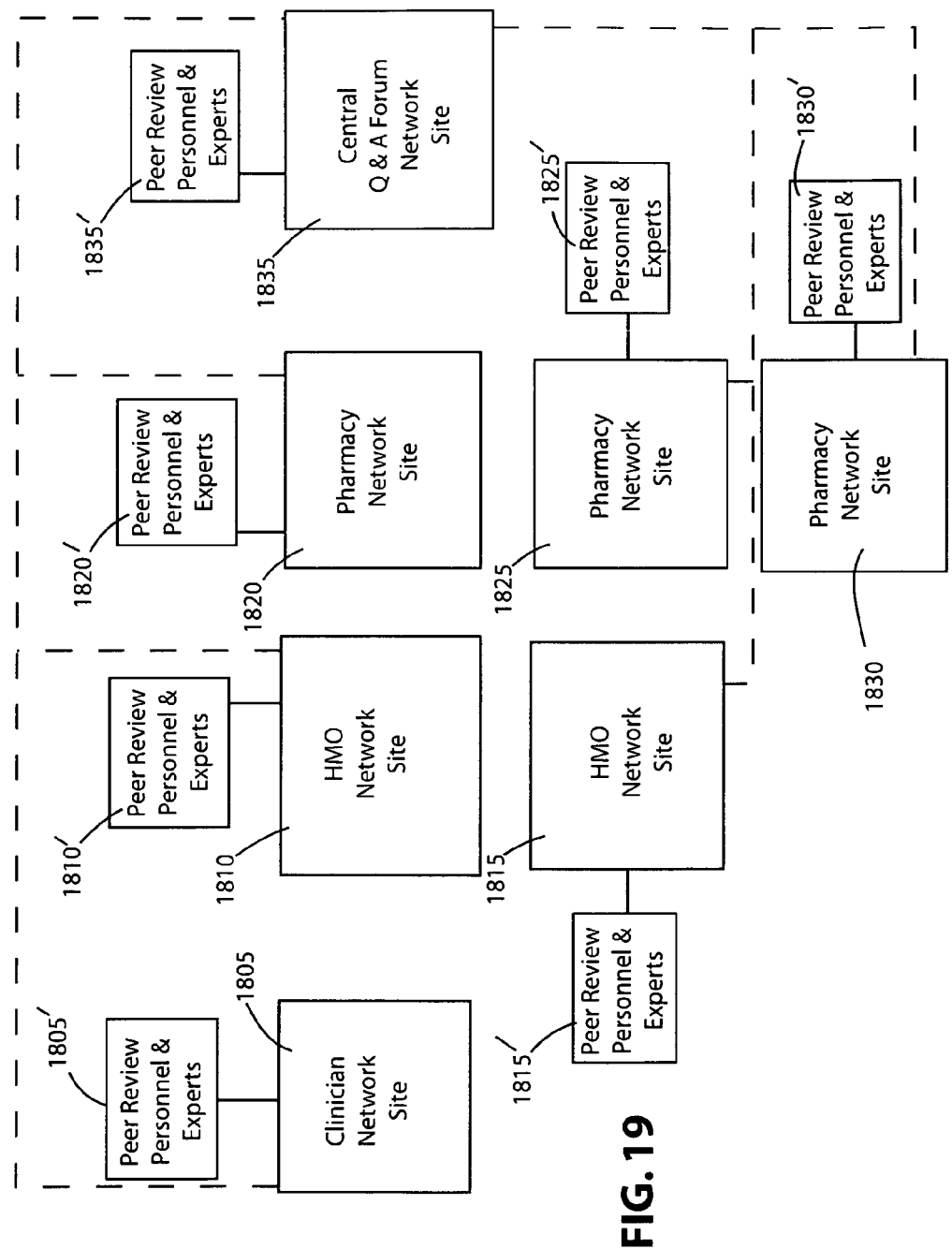
FIG. 19 is an exemplary block diagram of the system installed at multiple network sites, wherein each network site has its own localized peer review personnel and experts.
Figure 20:
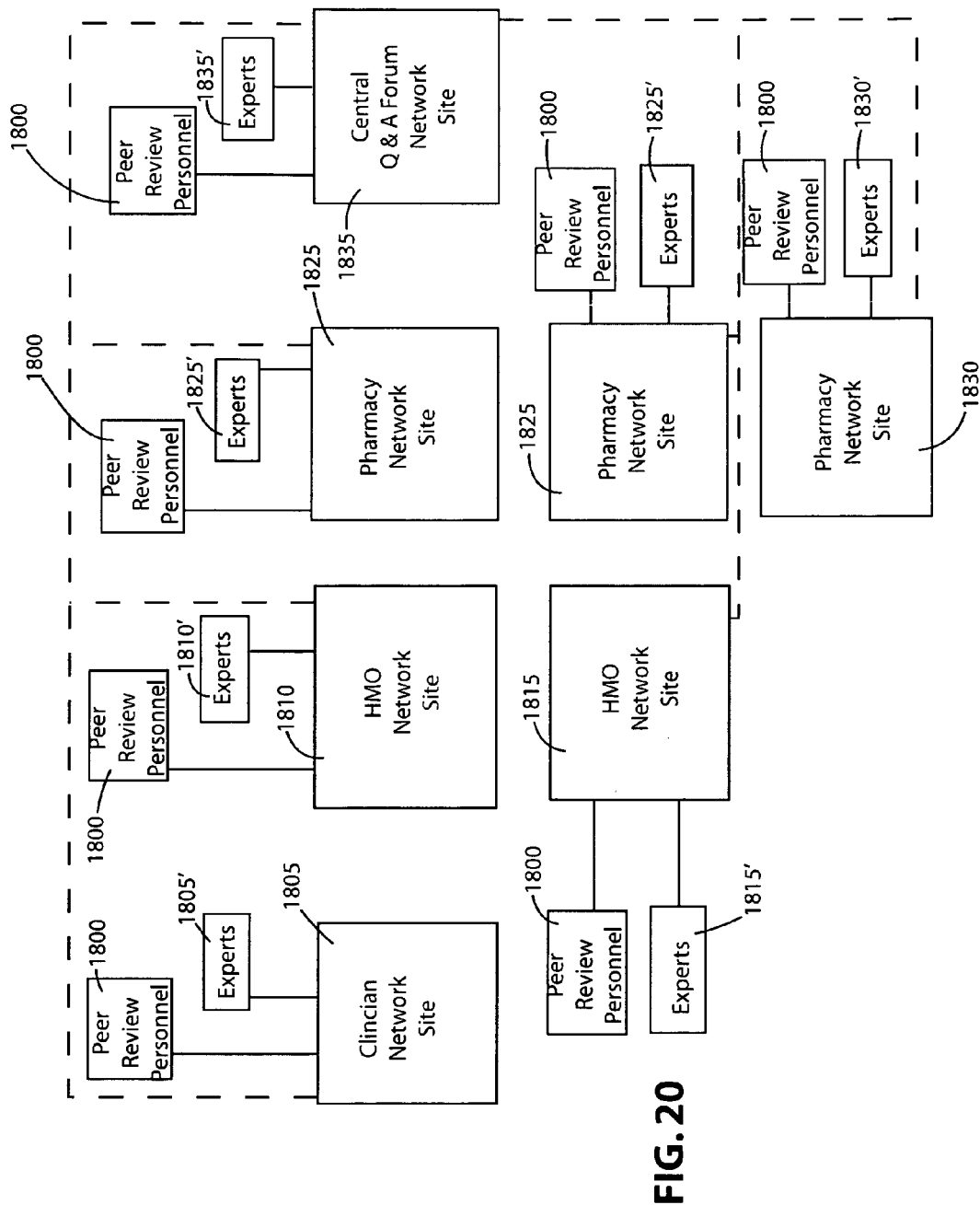
FIG. 20 is an exemplary block diagram of the system installed at multiple network sites, wherein each network site has its own experts but all network sites share a common pool of peer review personnel.

The functionality of the system deployed at each network site may be global or local. By way of example, in FIG. 18 the functionality is global in that the same pool of experts and peer review personnel 1800 may be used to respond and review questions generated by users at any of the network sites. In this case, irrespective of the network site at which a particular question is asked, the same experts and peer review personnel 1800 respond to and review the questions. Alternatively, each network site may select their own experts and peer review personnel to respond and review questions raised only by users and/or member of their network site. An exemplary embodiment of the localized selection of experts and peer review personnel is shown in FIG. 19. By way of example, an HMO network site may have a pool of experts that comprise only physicians affiliated with their HMO and the peer review personnel may be insurance case managers employed by that particular HMO. FIG. 20 is yet another exemplary embodiment, wherein each network site has its own localized selection of experts but all network sites share a common pool of peer review personnel 1800. It is evident that FIGS. 18-20 are only illustrative examples of some of the different configurations. Each network site can independently select: i) whether to establish a limited local pool of experts of their own choosing or use a common pool of global experts and ii) whether to establish a limited local pool of peer review personnel of their own choosing or use a common pool of global peer review personnel. This type of modularity allows each network site to opt in/out of globally sharing a common pool of experts and/or peer review personnel. Regardless of whether experts and/or peer review personnel have been locally selected by a particular network site to only answer questions originating from that network site, the experts and/or peer review personnel may post their responses in fora on other network sites in addition to posting their responses in fora on the network site from which the question originated. Accordingly, control over the distribution and dissemination of information resides exclusively with the experts and/or peer review personnel.

In an alternative embodiment, control over dissemination and distribution of information may lie exclusively with the operator of each network site. During initial configuration the particular network site may be programmed to prohibit the distribution and dissemination of information to and from other network sites. Thus, the operator of the network site can override an expert or peer review personnel command concerning on which network sites and fora to post their responses. Specifically, each network site may decide whether to post at their network site responses to user's questions generated at other network sites, and whether to permit the responses to questions generated by users at their network site to be posted at other network sites. Multiple permutations are therefore possible, since each network site may decide the following: (i) whether to rely on a group of global experts and/or peer review personnel or to select their own, (ii) whether to permit the posting of responses to questions generated at their network site on other network sites, and (iii) whether to post the responses to questions generated at other network sites on their network site. This type of modularity allows the operator of each network site to opt in/out of sharing experts, peer review personnel and/or information (e.g., questions and responses) with other network sites.

Although the invention has been described in detail in the foregoing embodiments, it is to be understood that they have been provided for purposes of illustration only and that other variations both in form and detail can be made thereupon by those skilled in the art without departing from the spirit and scope of the invention. In particular, although the operation of network site 114 is defined in terms of providing medical fora for access by the public, other types of fora may additionally or alternatively be provided, such as fora for the provision of financial advice, educational advice, career advice, or any other topic on which members of the public may seek expert opinions. Accordingly, the scope of the present invention shall not to be limited by the embodiments described above, but is to be defined solely by the appended claims.

What is claimed is:

1. A method implemented on a server for funding at least one interactive network site, the at least one interactive network site hosted by the server, presenting questions submitted by at least one of a plurality of users to at least one of at least two experts, the questions being submitted via at least one client interface, each client interface being identified to the users as a forum on a predetermined subject matter of the forum, at least one forum presenting the at least two experts as experts on the predetermined subject matter of the forum, the method comprising the steps of:
   the server receiving a question submitted by one of the plurality of users via the client interface of the at least one forum;
   the server routing the submitted question for presentation to one of the at least two experts;
   the server presenting the question to the one expert via one of a plurality of personal expert interfaces, each personal expert interface being uniquely associated with one of the at least two experts and in communication with the server;
   the server receiving a first command via the personal expert interface of the one expert, the first command including an instruction for the server to route the question to another one of the at least two experts via a personal expert interface of the other expert; and
   the server verifying receipt of a payment directed to fund access to the interactive network site by the one user, the payment being provided by a third party associated with a third party product or service.

2. The method in accordance with claim 1, wherein the third party provides an additional benefit for the one user, the additional benefit comprising at least one of a discount on a product, a medical treatment, a drug, an insurance premium, a deductible, or a co-payment contribution.

3. The method in accordance with claim 1, wherein the one user obtains access to the interactive network site by redeeming one or more points credited to the one user by the third party, wherein the one or more points have been credited to the one user as a result of the one user's consumption of a third party product or a third party service.

4. The method in accordance with claim 1, wherein:
   the third party provides a benefit in addition to the access-funding payment, the additional benefit concerning a third party product or service and being provided to a fourth party other than the third party, the user, and the expert.

5. The method in accordance with claim 4, wherein the third party is a drug manufacturer and the fourth party is one of a health maintenance organization and a pharmacy.

6. The method in accordance with claim 5, wherein the benefit to the fourth party is a discount on a drug.

7. The method of claim 1, wherein the first command is identified as representing a request for a second opinion and the third party product or service is one of a medical product or a medical service, further comprising the step of: the third party providing the one user with a discount on the third party product or service.

8. The method in accordance with claim 7, wherein the other expert is at least one of an insurance case manager, a representative of the third party or a medical professional.

9. The method in accordance with claim 8, wherein the other expert is at least one of an insurance case manager, a representative of the third party or a medical professional.

10. The method in accordance with claim 7, wherein the discount is applied to at least one of a medical insurance premium, a drug treatment, or a medical treatment.

11. The method in accordance with claim 7, further comprising the step of:
    the server receiving an answer via the personal expert interface of the one expert, wherein the first command further includes an instruction for the server to route the answer to the personal expert interface of the other expert.

12. The method in accordance with claim 1, wherein the first command is identified as representing a request for peer review, further comprising the steps of:
    the server receiving a first answer to the question via the personal interface of the one expert; and
    the server routing the first question and the first answer to the personal expert interface of the other expert for peer review of the first.

13. A method implemented on a server for funding at least one interactive network site hosted by the server, the at least one interactive network site providing answers to questions presented by a plurality of users, the users communicating with the server via a plurality of client interfaces, each of the client interfaces being identified to the users as a forum on a predetermined subject matter of the forum, the forum enabling users to present questions and to view questions and answers relating to the predetermined subject matter of the forum, the method comprising the steps of:
    generating at least two fora by the server on the at least one interactive network site;
    receiving a question at the server presented by a user accessing a first forum at one of the at least one interactive network site;
    posting the question by the server in a location on the server accessible to at least one expert;
    presenting the question by the server to the at least one expert via a personal expert interface of the at least one expert, said interface being unique to the at least one expert and on which the question is displayed for the at least one expert to answer;
    receiving at the server a command via the personal expert interface from the at least one expert in response to the question, wherein the command includes an answer responding to the question and an instruction;
    wherein the server posts the answer to the first forum accessed by the user to present the question; and the server further posts the answer to the question according to the instruction, wherein the instruction instructs that the answer be posted to at least a second one of the at least two forums at which the question was not presented by the user;
    displaying a banner advertisement for a third party by the server on a page of at least one client interface accessed by the plurality of users; and
    verifying receipt by the server of a payment for the banner advertisement by the third party, wherein an amount of the payment is determined by a monitoring of traffic on the network site by the server.

14. A method implemented on a server for funding at least one interactive network site hosted by the server, the at least one interactive network site providing answers to questions presented by a plurality of users, the users communicating with the server via a plurality of client interfaces, each of the client interfaces being identified to the users as a forum on a predetermined subject matter of the forum, the forum enabling users to present questions and to view questions and answers relating to the predetermined subject matter of the forum, the method comprising the steps of:
   generating at least two fora by the server on the at least one interactive network site;
   receiving a question at the server presented by a user accessing a first forum at one of the at least one interactive network site;
   posting the question by the server in a location on the server accessible to at least one expert;
   presenting the question by the server to the at least one expert via a personal expert interface of the at least one expert, said interface being unique to the at least one expert and on which the question is displayed for the at least one expert to answer;
   receiving at the server a command via the personal expert interface from the at least one expert in response to the question, wherein the command includes an answer responding to the question and an instruction; wherein the server posts the answer to the first forum accessed by the user to present the question; and the server further posts the answer to the question according to the instruction, wherein the instruction instructs that the answer be posted to at least a second one of the at least two forums at which the question was not presented by the user; and
   verifying receipt by the server of a payment by a third party, wherein the third party is a sponsor of at least one of the first forum or the second forum.

15. The method in accordance with claim 14, wherein the at least one expert is presented simultaneously as an expert in at least the first forum and the second forum.

16. The method in accordance with claim 15, wherein the question requests a second opinion in regard to a medical treatment being received by the user, and the at least one expert is a peer reviewer applying review criteria selected by the third party sponsor for providing the second opinion.

17. The method in accordance with claim 15, wherein the question requests a second opinion in regard to a medical treatment being received by the user, and the at least one expert is a peer reviewer applying review criteria established independently of the third party sponsor for providing the second opinion.

18. The method in accordance with claim 15, wherein the at least one expert is one of an employee or a contractor of the third party sponsor.

19. The method in accordance with claim 15, wherein the third party sponsor is a pharmaceutical manufacturer and the at least one interactive network site includes at least one of a drug retailer network site or a health maintenance organization network site.

20. A method implemented on a server for funding at least one interactive network sites site hosted by the server, the at least one interactive network site providing answers to questions presented by a plurality of users, the users communicating with the server via a plurality of client interfaces, each of the client interfaces being identified to the users as a forum on a predetermined subject matter of the forum, the forum enabling users to present questions and to view questions and answers relating to the predetermined subject matter of the forum, the method comprising the steps of:
   the server generating at least two forums in the at least one interactive network site;
   the server sending a question presented by a user accessing a first one of the at least two forums to a first expert via a personal expert interface of the first expert, the personal expert interface of the first expert being a web page unique to the first expert on which the question is displayed;
   the server receiving a first response to the question from the first expert, the first response including an answer to the question and a first instruction to post the answer to the question;
   the server posting the answer to the question to the first forum accessed by the user to present the question; and in response to the first instruction, further posting the answer to the question, according to the first instruction, to a second one of the at least two forums, at which the question was not presented by the user; and
   the server verifying receipt of a payment by a third party for funding the posting of the response, the third party identified as being associated with at least one of the at least two forums.

21. The method in accordance with claim 20, wherein the payment includes paying a fee for the user to access the forum.

22. The method in accordance with claim 20, further comprising the steps of:
   the server receiving a second response to the question from the first expert, the second response including a second instruction to refer the question;
   the server, in response to the second instruction, referring the question to a second one of the plurality of experts; and
   the server receiving a response from the second expert that provides a-supplemental answer to the question.

23. The method in accordance with claim 22, wherein the second expert is a peer reviewer and the supplemental answer provides a review of the first response to the question from the first expert.

24. The method in accordance with claim 23, wherein the first instruction instructs that the response from the second expert be posted only on the first forum from which the question originated.

25. The method in accordance with claim 23, wherein the first instruction instructs that the response from the second expert be posted on the first forum from which the question originated and on at least one other forum on one other network site.

26. The method in accordance with claim 20, wherein:
   the third party provides a benefit in addition to the funding payment, the additional benefit concerning a third party product or service and being provided to a fourth party other than the third party, the user, and the expert.

27. The method in accordance with claim 26, wherein the third party is a drug manufacturer and the fourth party is one of a health maintenance organization and a pharmacy.

28. The method in accordance with claim 27, wherein the benefit to the fourth party is a discount on a drug.

* * * * *

UNITED STATES PATENT AND TRADEMARK OFFICE
CERTIFICATE OF CORRECTION

PATENT NO. : 7,596,578 B1  
APPLICATION NO. : 09/603601  
DATED : September 29, 2009  
INVENTOR(S) : James D. Marks Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1051 days.

Signed and Sealed this

Twenty-eighth Day of September, 2010

David J. Kappos  
*Director of the United States Patent and Trademark Office*